United States Patent
Soo

(10) Patent No.: US 9,782,337 B2
(45) Date of Patent: Oct. 10, 2017

(54) METHODS AND COMPOSITIONS USING COMPOUNDS FROM FETAL CELLS AND TISSUES TO IMPROVE CONDITION OF SKIN

(75) Inventor: Chia Soo, Beverly Hills, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 868 days.

(21) Appl. No.: 11/929,627

(22) Filed: Oct. 30, 2007

(65) Prior Publication Data

US 2008/0152639 A1    Jun. 26, 2008

Related U.S. Application Data

(63) Continuation of application No. 10/733,150, filed on Dec. 10, 2003, now abandoned.

(60) Provisional application No. 60/432,519, filed on Dec. 11, 2002.

(51) Int. Cl.
| | |
|---|---|
| *A61K 35/48* | (2015.01) |
| *A61K 8/73* | (2006.01) |
| *A61L 15/40* | (2006.01) |
| *A61Q 19/00* | (2006.01) |
| *A61Q 19/08* | (2006.01) |

(52) U.S. Cl.
CPC .............. *A61K 8/735* (2013.01); *A61K 8/73* (2013.01); *A61K 35/48* (2013.01); *A61L 15/40* (2013.01); *A61Q 19/00* (2013.01); *A61Q 19/08* (2013.01)

(58) Field of Classification Search
CPC .......... A61K 35/48; A61K 8/73; A61K 8/735; A61L 15/40; A61Q 19/00; A61Q 19/08; G03B 31/00
USPC ........ 369/115; 424/94.6; 514/18.6, 20.9, 54, 514/9.1
See application file for complete search history.

(56) References Cited

U.S. PATENT DOCUMENTS

| | | | |
|---|---|---|---|
| 5,510,328 A | 4/1996 | Polarek et al. | |
| 5,583,103 A | 12/1996 | Ruoslahti et al. | |
| 5,654,270 A | 8/1997 | Ruoslahti et al. | |
| 5,851,994 A | 12/1998 | Schreiber et al. | |
| 6,509,314 B1 | 1/2003 | Ruoslahti et al. | |
| 7,056,711 B2* | 6/2006 | Denholm et al. | 435/183 |
| 2003/0032591 A1 | 2/2003 | Ruoslahti et al. | |
| 2003/0124152 A1* | 7/2003 | Pang | 424/401 |

FOREIGN PATENT DOCUMENTS

| | | |
|---|---|---|
| DE | 41 20083 | 12/1992 |
| WO | WO 93/09800 | 5/1993 |
| WO | WO 9309800 A1 * | 5/1993 |
| WO | WO 00/40227 | 7/2000 |
| WO | WO 02/41865 | 5/2002 |

OTHER PUBLICATIONS

Danielson et al. Feb. 10, 1997 // JCB vol. 136, No. 3, 729-743.*
Ezura et al. The Journal of Cell Biology, vol. 151, No. 4, Nov. 13, 2000 779-787.*
Adzick, N.S. et al., *Cells, Matrix, Growth Factors, and the Surgeon: The Biology of Scarless Fetal Wound Repair*, Annals of Surgery, 1994, vol. 22, No. 1, pp. 10-18.
European Search Report for 03812980.5, mailed May 23, 2006, 5 pgs.
European Search Report for 03812980.5-2103, mailed Sep. 13, 2006, 7 pgs.
Lee, T.Y. et al., *Endogenous Expression of Matrix Metalloproteinases 7 and 9 and their Tissue Inhibitors as a Function of Gestational Age in Fetal Rat Skin*, Surgical Forum, 1998, vol. 49, pp. 464-466.
Lorenz, H.P. et al., *Differential Expression of Matrix Metalloproteinases and their Tissue-Derived Inhibitors in Scarless Fetal Wound Healing*, Surgical Forum 2001, vol. 52, pp. 397-401.
Saika et al., "Role of Lumican in the Corneal Epithelium during Wound Healing", the J. of Biological Chem. vol. 275, No. 4, pp. 2607-2612, 2000.
Shafritz, T.A. et al., *Specific Effects of Glycosaminiglycans in an Analog of Extracellular Matrix that Delays Wound Contraction and Induces Regeneration*, Wound Repair and Regeneration, 1994, vol. 2, pp. 270-276.
Soo et al., Differential Expression of Fibromodulin, a Transforming Growth Factor-Beta Modulator, in Skin Development and Scarless Repair, American J. Pathology, vol. 157, No. 2, pp. 423-433, 2000.
Soo, C. et al., *Differential Expression of Fibromodulin, a Transforming Growth Factor-Beta Modulator, in Fetal Skin Development and Scarless Repair*, American J Pathology, Aug. 2000, vol. 157, No. 2, pp. 423-433.
Supplementary European Search Report for Application No. 03812980.5-2013, mailed Sep. 13, 2006 (8 pages).
Danielson, K. G. et al, "Targeted Disruption of Decorin Leads to Abnormal Collagen Fibril Morphology and Skin Fragility", JCB, vol. 136, No. 3, pp. 726-743 (1997).
Ezura, Y. et al., "Differential Expression of Lumican and Fibromodulin Regulate Collagen Fibrillogenesis in Developing Mouse Tendons", The Journal of Cell Biology, vol. 151, No. 4, pp. 779-787 (2000).

* cited by examiner

*Primary Examiner* — Janet Epps-Smith
(74) *Attorney, Agent, or Firm* — Duane Morris LLP

(57) ABSTRACT

Compositions comprising one or more compounds expressed by fetal tissues for modulating skin conditions, methods of identifying the compounds, and methods of making and using the compounds are provided.

20 Claims, 13 Drawing Sheets

METHODS AND COMPOSITIONS USING COMPOUNDS FROM FETAL CELLS AND TISSUES TO IMPROVE CONDITION OF SKIN

CROSS-REFERENCE TO RELATED APPLICATIONS

The application is a continuation of U.S. application Ser. No. 10/733,150, filed on Dec. 10, 2003, now abandoned, which is a non-provisional application of U.S. provisional application Ser. No. 60/432,519, filed on Dec. 11, 2002. The teachings of both applications are incorporated herein in their entirety by reference.

FIELD OF THE INVENTION

The present invention relates to cosmetic skin care compositions containing compounds expressed by fetal cells and tissues that promote the condition of skin. The present invention also relates to methods of identifying and producing compounds expressed by fetal cells and tissues. The present invention also relates to methods and compounds to promote the condition of skin utilizing proteoglycans, which includes fibromodulin (FM), or any functionally equivalent compound.

BACKGROUND OF THE INVENTION

Skin, among other things, is composed of epidermal and dermal layers. The dermal layer provides the support and blood supply for the epidermis. The dermal layer is also important in maintaining the elasticity and appearance of the skin. The dermis is largely comprised of cells and extracellular matrix ("ECM"). The composition of the ECM is largely determined by fibroblasts that elaborate various components such as collagens, elastins, and proteoglycans. With increasing age, as well as exposure to the sun and environmental contaminants, there is progressive thinning and disruption of the supporting dermis. This leads directly to sagging and consequent furrowing of the epidermis, i.e., the formation of wrinkles. (See, for example, Oikarinen A. The aging of skin: chronoaging versus photoaging. *Photodermatol Photoimmunol Photomed* 7: 3-4, 1990).

It is well established in the art that fetal skin is fundamentally different from adult skin. For instance, after injury, adult skin repairs through scar formation, a process characterized by the replacement of injured tissues with a disorganized deposition of collagen and various ECM components, referred to collectively as a "scar." In contrast, fetal skin repair occurs by cellular regeneration and restoration of normal skin architecture through organized deposition of collagen and ECM components to effect scarless repair. Studies have shown that the capabilities for scarless skin repair is one quality of fetal skin, and does not require the fetal immune system, fetal serum, or amniotic fluid (Bleacher J C, et al., *J Pediatr Surg* 28: 1312-4, 1993); Ihara S, Motobayashi Y., *Development* 114: 573-82. 1992). For example, isolated human fetal skin transplanted into athymic mice heals without producing typical scar tissue (Adzick N S, Lorenz H P., *Ann Surg* 220: 10-8. 1994).

Accordingly, it appears that specific molecules or compositions in regenerating fetal skin that are minimally present or not present at all in non-fetal skin (e.g., adult skin) are important in regenerating and promoting the appearance of skin.

Numerous compounds and techniques have been described in the art as being useful for promoting the condition of skin, especially of "aged" or wrinkled skin. Topical compounds include retinoic acid for stimulation of epidermal cell growth. Retinoids are well recognized as anti-wrinkle actives which help to reduce the subcutaneous effects of aging such as wrinkling, leatheriness, looseness, roughness, dryness, and mottling (hyper pigmentation) (see, U.S. Pat. Nos. 4,603,146 and 4,877,805). It has been postulated that retinoids act by producing inflammation, which causes thickening of the epidermis (acanthosis), and local intercellular edema, leading to exfoliation and improved skin texture and appearance. Use of L-ascorbic acid to stimulate fibroblast cell growth and collagen production has also been described (Hata R, Senoo H. *J Cell Physiol* 138:8-16. 1989). Techniques for promoting the condition of skin include deliberate methods of inducing skin irritation/injury through chemical (e.g., phenol peels), mechanical (e.g., dermabrasion), or thermal (e.g., lasers) means. Injury to the epidermis and/or dermis ultimately results in new cell growth and ECM deposition that may improve the overall appearance of skin.

Another skin conditions that often lead to skin damages is inflammation. In principle, the inflammatory and immune responses can be regulated through the use of drugs (In Goodman & Gilman's *The Pharmacological Basis of Therapeutics* eds. Hardman et al., Ninth Edition, McGraw-Hill publishing, 1996). Glucocorticoids and aspirin-like drugs (non-steroidal anti-inflammatory agents, NSAIDs) are the most widely used anti-inflammatory agents. NSAIDs are typically used to treat symptoms of inflammation (e.g. pain and fever). Corticosteroids are effective anti-inflammatory agents, having effects on virtually all inflammatory cells, but manifest significant adverse effects, such as inducing Cushingoid features, skin thinning, increased susceptibility to infection, effects on wound healing, and suppression of the hypothalamic-pituitary-adrenal axis. Other anti-inflammatory drugs presently available produce cytotoxic effects that reflect their initial employment as cancer chemotherapeutics, typically anti-neoplastic agents. Such drugs may kill cells indiscriminately, particularly those that proliferate rapidly. Methotrexate, however, is effective in treating rheumatoid arthritis at doses lower than those used to treat cancer (cytoreductive dose). Immunosuppressive agents, such as cyclosporin A and tacrolimus, are effective in preventing allograft rejection, but their use in treating autoimmune diseases has been limited by the development of severe side effects, particularly nephrotoxicity.

With specific regard to skin, topical or oral corticosteroids or antihistamines are the mainstays of therapy. However, corticosteroids have many undesirable side effects as listed above, while antihistamines may themselves elicit an allergic reaction when applied topically or cause excessive drowsiness when taken orally (Shai A, et al., Inflammation, dermatitis and cosmetics. *Handbook of Cosmetic Skin Care*. London: Martin Dunitz Ltd., pp. 135-146, 2001).

Hyperpigmentation is another common skin disease. Once present, hyperpigmentation is very difficult to treat. Because acquired hyperpigmentation can have a significant negative impact on cosmetic and psychosocial issues, much attention has focused on the treatment of hyperpigmentation. The current state of the art in hyperpigmentation offers many modalities, but none are completely satisfactory. The major limitation is that current modalities are primarily skin "bleaching" compounds that are fairly ineffective at treating established hyperpigmentation, especially dermal hyperpigmentation (Reviewed in Briganti S, et al., *Pigment Cell Res.*

16: 101-110, 2003). A variety of other substances have been proposed for the control or inhibition of skin pigmentation. Almost all of these substances work by either bleaching existing pigment or preventing new pigment synthesis by inhibiting the activity of tyrosinase, the principle rate-limiting enzyme in the production of melanin. For example, U.S. Pat. No. 6,123,959 describes the use of aqueous compositions comprising liposomes and at least one competitive inhibitor of an enzyme for the synthesis of melanin in combination with at least one non-competitive inhibitor of an enzyme for the synthesis of melanin. U.S. Pat. No. 6,132,740 describes the use of certain resorcinol derivatives as skin lightening agents. WO 99/64025A1 describes compositions for skin lightening which contain tyrosinase inhibiting extracts from dicotyledonous plant species indigenous to Canada. U.S. Pat. No. 5,580,549 describes an external preparation for skin lightening comprising 2-hydroxybenzoic acid derivatives and salts thereof as inhibitors of tyrosinase. WO 99/09011A1 describes an agent for inhibiting skin erythema and/or skin pigmentation, containing at least one carbostyril derivative and salts thereof. U.S. Pat. Nos. 5,214,028 and 5,389,611 describes lactoferrin hydrolyzates for use as a tyrosinase inhibitory agents. Additionally, a number of compounds and plant extracts are reported to have activity against hyperpigmentation, including ascorbic acid and derivatives thereof, kojic acid and compounds related thereto, licorice (glycyrrhiza) extract, and bearberry extract. While these chemical compounds and extracts are active in the reversal and prevention of hyperpigmentation, they can be irritating to the skin with prolonged use.

Despite the proposal of all these substances, the main products for treatment of hyperpigmentation contains hydroquinone, a well known active substance for skin de-pigmentation (e.g., see U.S. Pat. No. 6,139,854). However, hydroquinone can have serious side effects if applied over a long period of time. For example, the application of hydroquinone to skin may lead to permanent de-pigmentation, and thus to increased photosensitivity of the skin when exposed to ultraviolet light. Moreover, hydroquinone can be metabolized to benzoquinones, which are potent haematotoxic, genotoxic and carcinogenic compounds that can also induce the formation of radical species, predisposing cells to oxidative damage (Do Ceu Silva M, et al., *Mutagenesis*. 18:491-496, 2003). For that reason, in some countries hydroquinone is only allowed to be used for skin de-pigmentation in limited concentrations, and, in other countries, the product is banned completely for this application.

Therefore, there is a need for new and more effective methods for modulating skin conditions such as treating skin aging, inflammation and pigmentation which carry fewer significant and undesirable side effects.

SUMMARY OF THE INVENTION

Described herein are novel cosmetic skin care compositions containing compounds expressed by fetal tissues to promote the condition of skin. The compounds may be delivered to skin by way of, but not limited to, a solution, a lotion, an ointment, a cream, a gel, or a skin peelable strip.

Although individual identification or purification of compounds expressed by fetal tissues may be useful, the application of this invention does not require the individual identification or purification of the compounds. The present invention also relates to methods of identifying compounds expressed by fetal tissues or of identifying the conditions that promote expression of these compounds. The present invention also relates to methods for promoting expression of compounds expressed by fetal tissues through modification of external cellular environments or through recombinant expression.

The present invention also relates to methods of using compositions containing compounds expressed by fetal tissues to improve the condition of skin. The methods generally include the step of topically applying the composition to the skin of a mammal in need of treatment and where a safe and effective amount of the compositions is used.

Furthermore, the present invention describes novel cosmetic skin care compositions containing a safe and effective amount of FM, or functionally equivalent molecule in purified or enriched extract form.

Other components which may be included with the compositions containing compounds expressed by fetal tissues or FM, depending on the formula, are safe and effective amounts of hyaluronic acid, an additional skin care active, and a cosmetically acceptable, dermatologically acceptable or pharmaceutically acceptable carrier.

Representative embodiments of the compositions include, but are not limited to hyaluronic acid, ECM peptides or polypeptides, growth factors, and L-ascorbic acid.

These and other features, aspects, and advantages of the present invention will become evident to those skilled in the art from a reading of the present disclosure.

There is moderate inflammatory infiltrate and increased red blood cells. B. 24 hours post-injury, 400×. Re-epithelialization is also noted at 24 hours after injury (black open arrow). C. 24 hours post-injury, 400×. Monocytes (black open arrows) comprises most of the inflammatory cells. D. 72 hours post-injury, 100×. The wound is completely re-epithelialized with increased cellularity and neovascularity. Hair follicles (black open arrows) are not observed in the repaired wound site (far left) compared with unwounded site (far right). E. 72 hours post-injury, 400×. At higher magnification, blue vital dye (black open arrows) within the repaired wound is visible. F. Confocal microscopic view of E19 rat skin (Fa through Fc). Fa. 48 hours post-injury, 630×. Large spaces among newly formed collagen fibers within the dermis are noticeable. A thin layer of dense collagen fibers is seen as basement membrane (white open arrows). Fb. 72 hours post-injury, 630×. Disorganized collagen deposition pattern with heterogeneously sized collagen fibers is apparent in the healed dermal scar tissue. Note the absence of hair follicle regeneration. Fc. Non-wounded neonatal day 1 (N1) skin [i.e., E19+72 hours, E21=term], 630×. Non-wounded N1 skin exhibited an organized collagen deposition pattern that is significantly different from E19 skin, 72 hours post-wounding. e: epidermis. h: hair follicle. d: dermis. Scale bars: A,D, 200 µm; B,C,E, 50 µm; Fa-Fc, 32 µm. G. There is significantly increased total collagen density in wounded E19 fetuses 72 hours post-injury relative to non-wounded N1 controls (p=0.00043).

Figure 4:
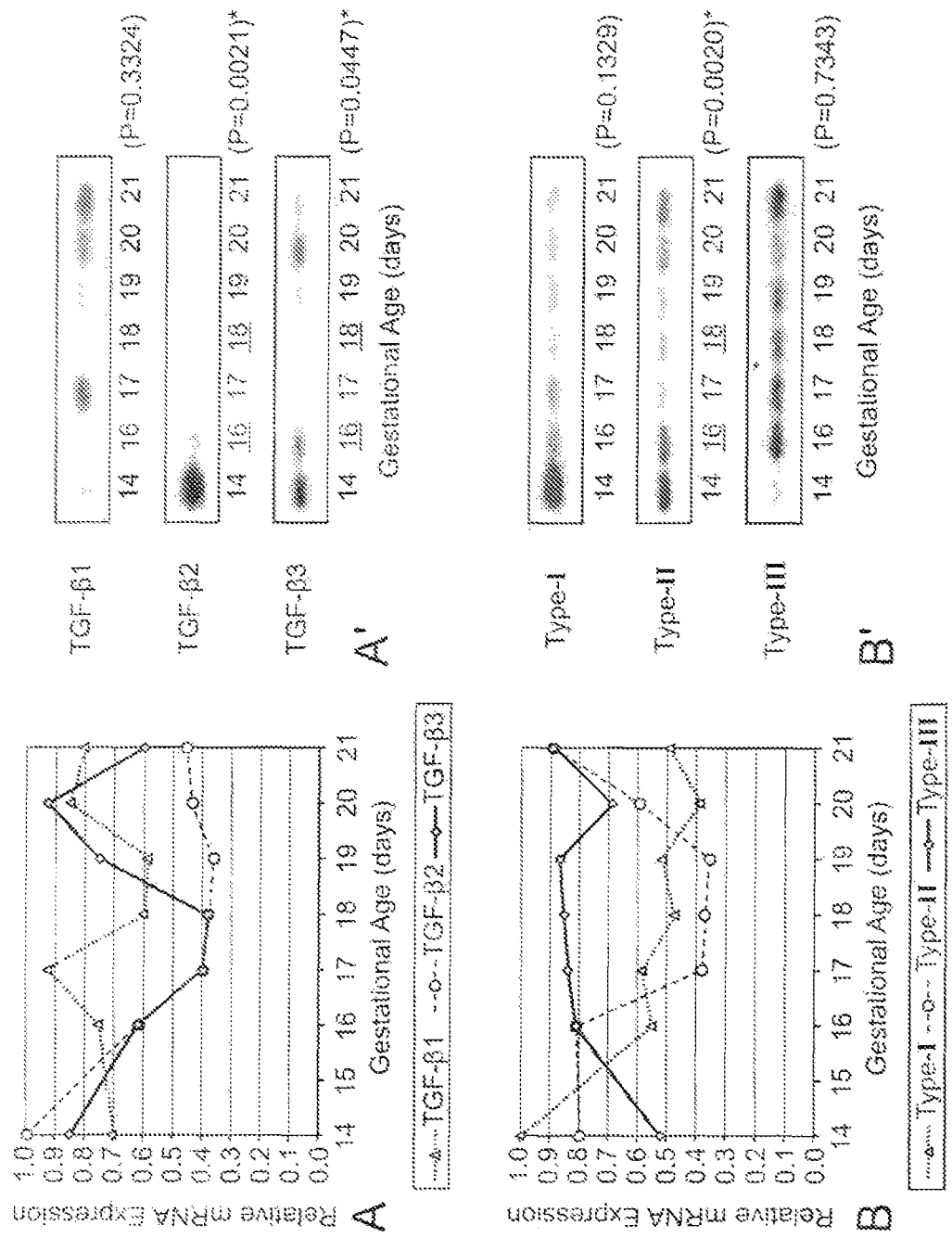
Figure 4:
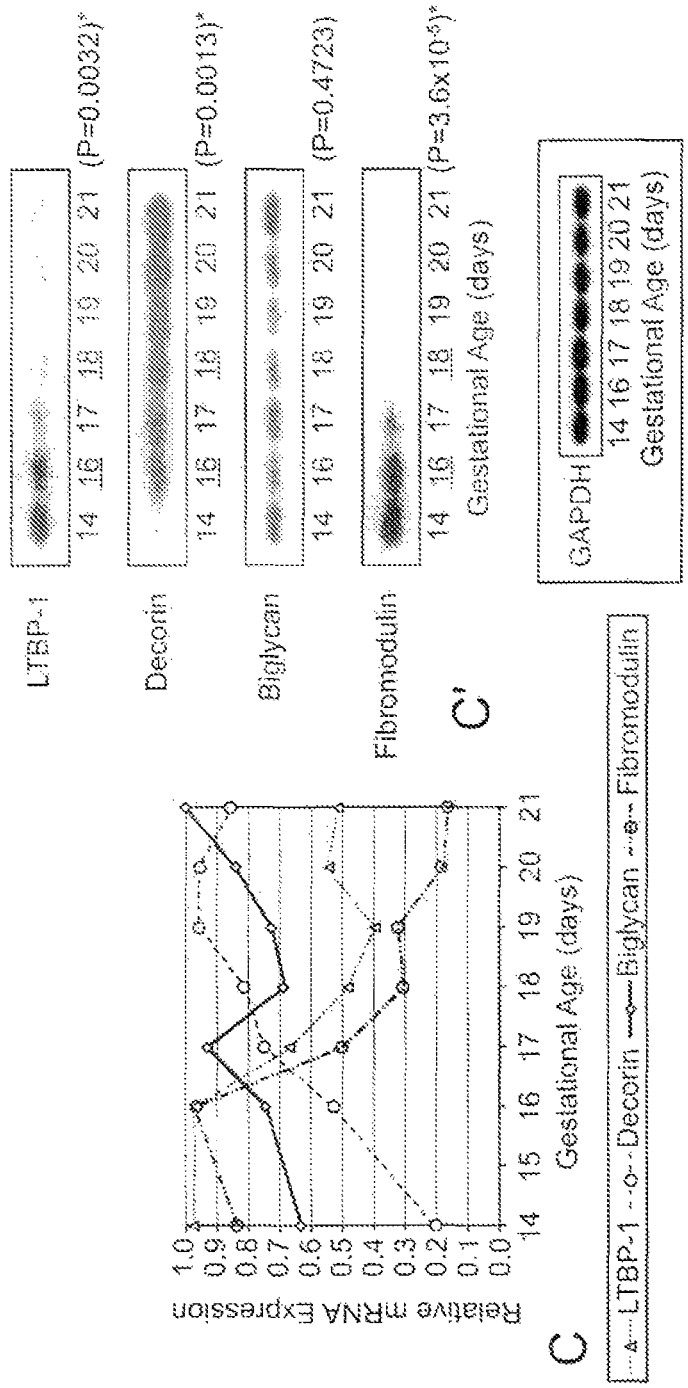

FIG. 4 shows specific primer based reverse transcription polymerase chain reaction (RT-PCR) screening of gene expression for transforming growth factor (TGF)-β ligands, receptors, and modulators during fetal skin development. RT-PCR was performed on RNA isolated from day 14, 16, 17, 18, 19, 20, and 21 fetal dorsal skin (N=10-15 fetuses/time point). To determine relative changes in mRNA levels during development, densitometry values for each blot were corrected to GAPDH expression at each time point and normalized by setting the highest value to one. The results are depicted graphically as the mean (A,B,C). The transition period is highlighted in gray. Unpaired two-tailed student's t test was performed to detect statistically significant differences in gene expression between E16 (beginning transition) and E18 (end transition) fetal skin. A representative blot is shown for each TGF-β ligand (A'), receptor (B'), or modulator (C') with the corresponding P value on the right and the transition period highlighted in gray. Statistically significant differences in gene expression between day 16 (beginning transition) and day 18 (end transition) fetal skin are underlined (A',B',C'). Statistically significant P values (<0.05) are marked with an "*". A representative fetal GAPDH PCR reaction is shown (inset).

Figure 5:
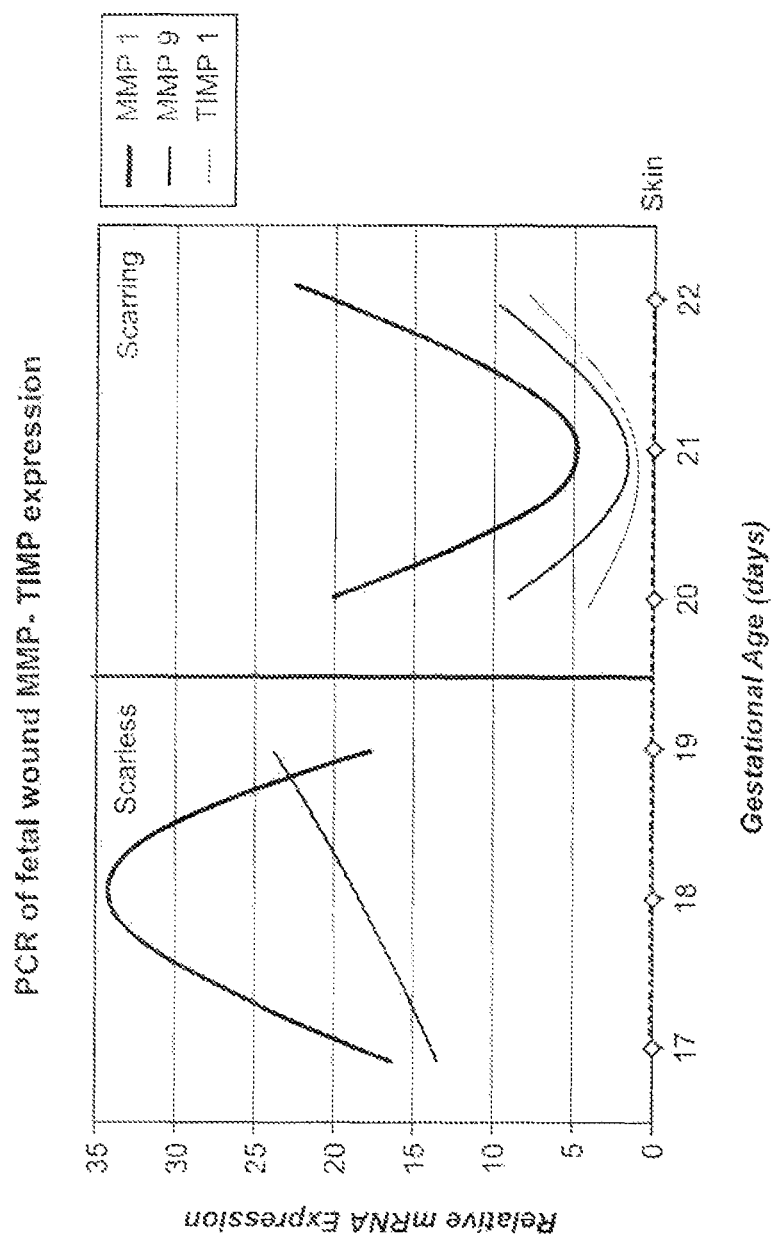

FIG. 5 shows graphically specific primer based RT-PCR screening of gene expression for matrix metalloproteinases (MMP) and their tissue-derived inhibitors (TIMPs) during repair. In general, wounds that scar have a relative propensity towards excessive ECM deposition rather than degradation (right), while scarless wounds have a relative propensity towards less ECM deposition.

Figure 6:
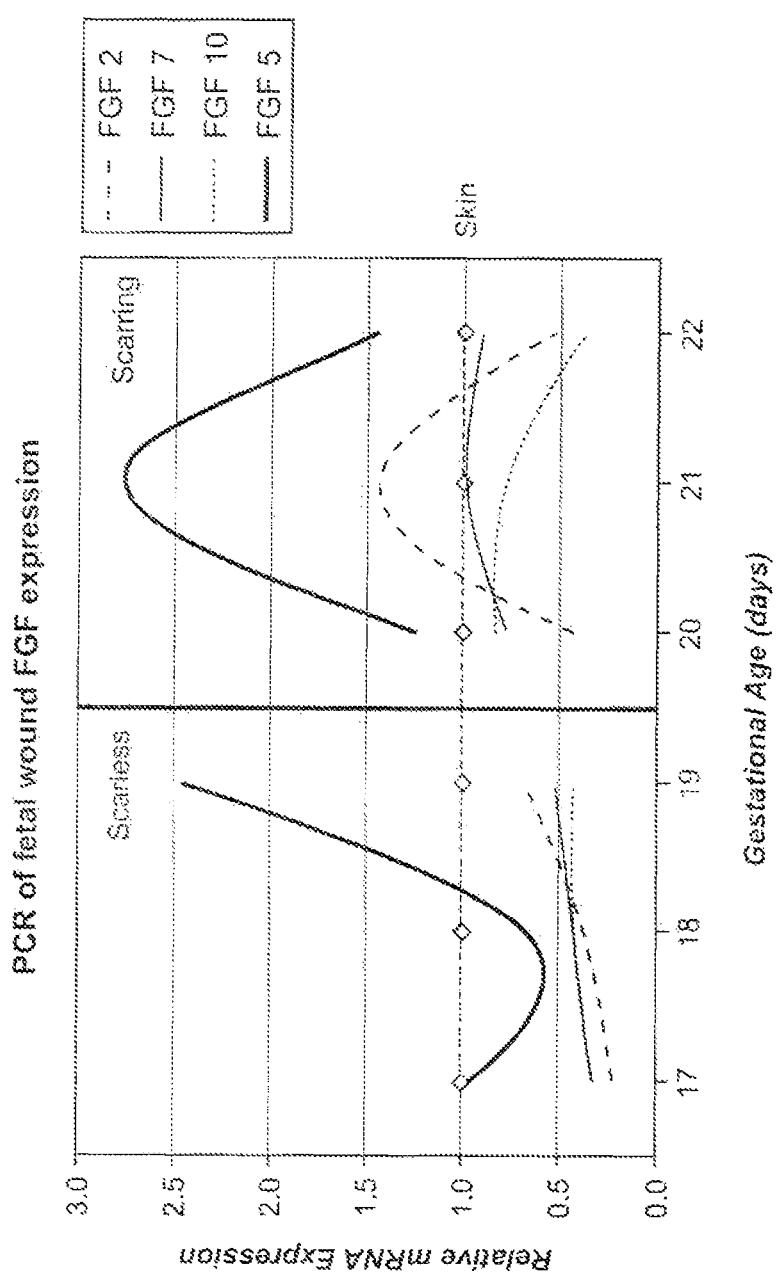

FIG. 6 shows graphically specific primer based RT-PCR screening of gene expression for FGFs during repair. In general, wounds that scar appear to be associated with higher bFGF (FGF-2) expression (right), while scarless wounds have relatively less bFGF expression.

Figure 7A:
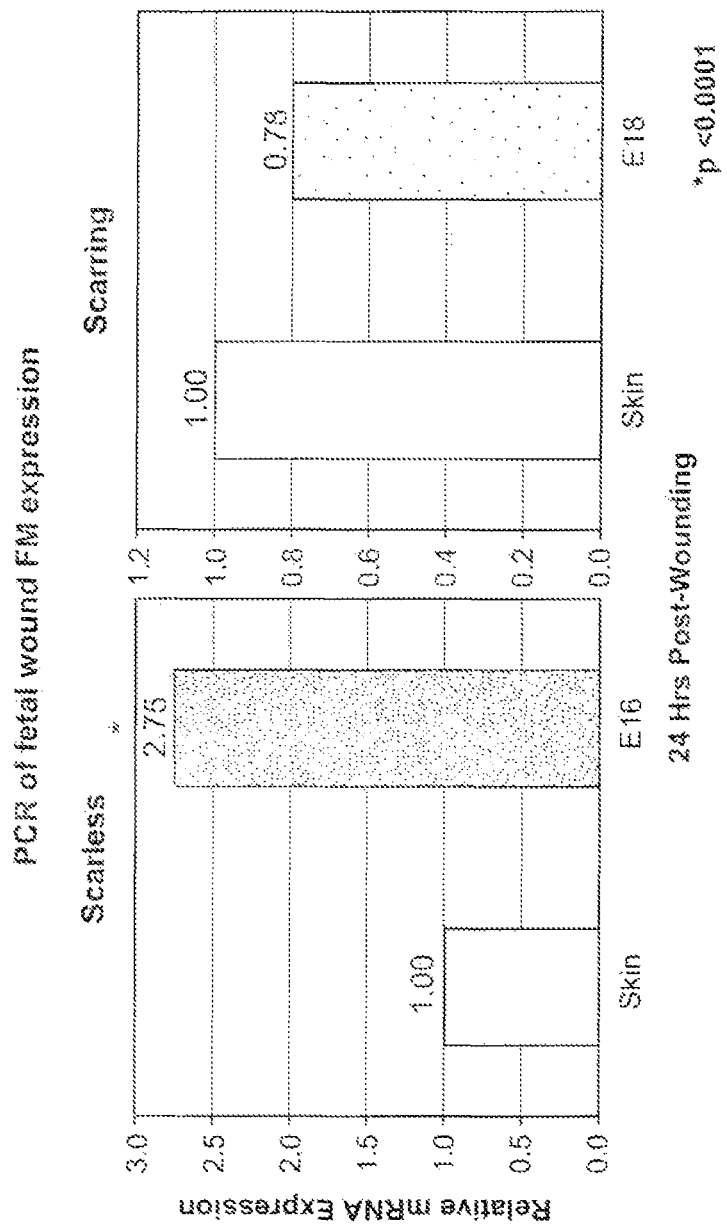

FIGS. 7A and B show graphically specific primer based RT-PCR screening of gene expression for FM and decorin during repair. A. FM transcripts increased markedly by 2.75-fold 24 hours after injury in E16 fetuses (P<0.0001) that manifest regenerative repair, but not in E18-wounded fetuses with non-regenerative repair. B. In contrast, decorin transcripts are relatively higher in E18 wounds when compared to E16 wounds, although both E16 and E18 wounds displayed decreased decorin levels relative to non-wounded aged match controls.

Figure 8:
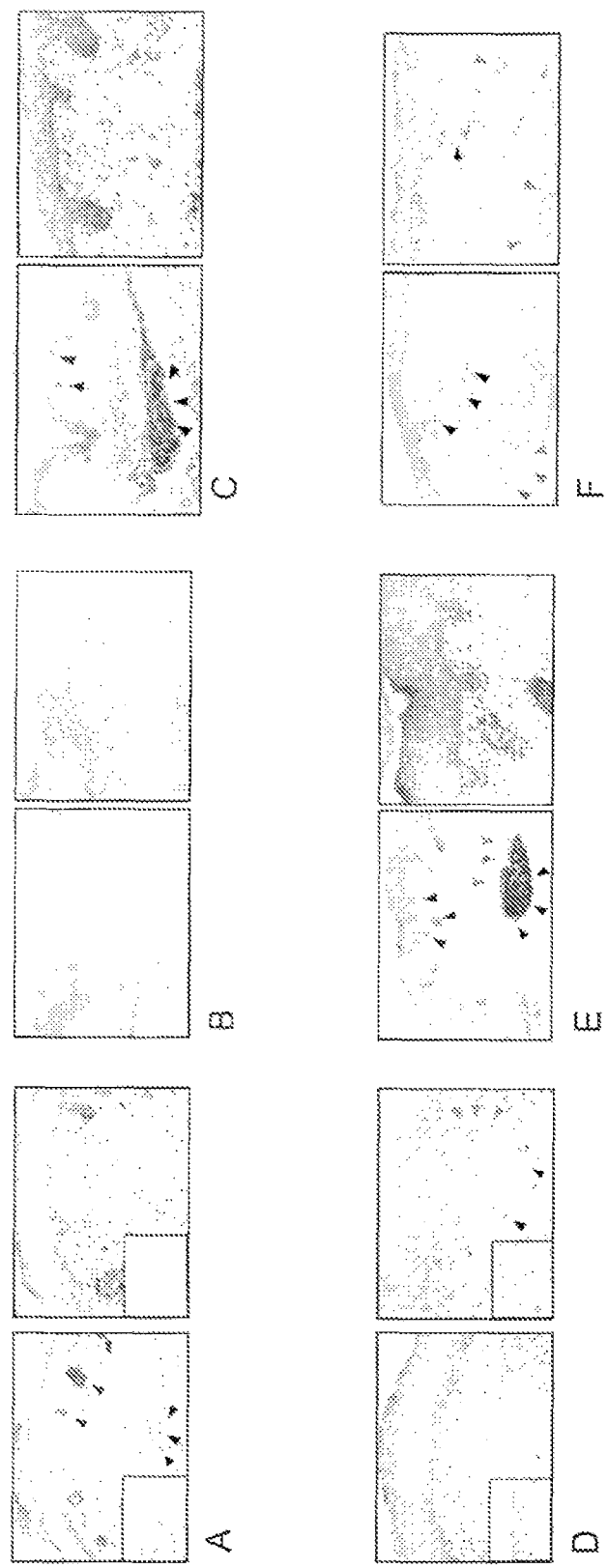

FIG. 8. shows the results of applying and blocking compounds identified through gene screening of fetal skin. In this case the compound is FM. H&E staining shows that FM application to late gestation wounds that normally heal without regeneration results in complete scarless regenerative repair, while and anti-FM antibody application to early gestation wounds that normally heal with scarless regeneration results in non-regenerative repair. Wounds, shown at 200× (left) and 400× (right) magnification, were harvested at 72 hours along with controls. Red arrows indicate permanent dye. Black arrows indicate hair follicles. A. Normally, (E16) fetal wounds heal scarlessly and would be indistinguishable from control (E19) skin (insets), if not for the presence of permanent dye and disruption of the panniculus carnosus muscle (blue arrows). Note the regeneration of hair follicles and absence of inflammation. B. Treatment of E16 wounds with anti-FM antibody induced scar formation. Hair follicles have failed to regenerate and inflammation is present. C. Treatment of E16 fetal wounds with an immunoglobulin G (IgG) control solution failed to induce scarring. Note the hair follicles. D. Usually, E18 fetal wounds heal with scar. In the scar, inflammatory cells (blue arrows) are present, but hair follicles are absent. E. Treatment of E18 fetal wounds with exogenous FM inhibited scar formation. These wounds can only be identified by permanent dye and disruption of the panniculus carnosus muscle (blue arrows), since they lack significant inflammation and contain hair follicles. F. E18 wounds treated with the collagen control solution still healed with scar formation. Note the inflammatory cells (blue arrows) and absence of hair follicles.

Figure 9:
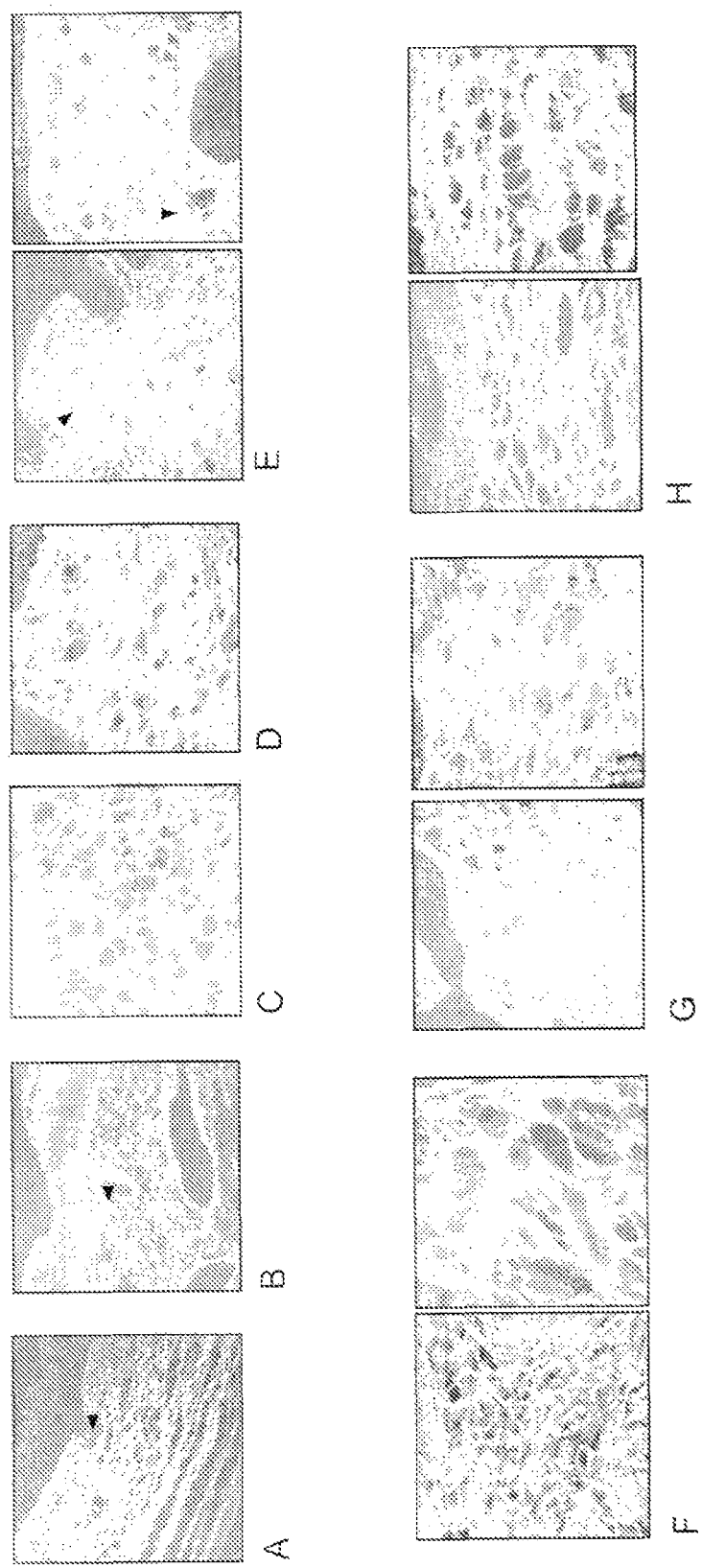

FIG. 9. shows confocal microscopy of FM and anti-FM antibody treated fetal wounds. FM treated late gestation wounds demonstrate an organized collagen architecture, while anti-FM antibody treated wounds demonstrate a disorganized collagen architecture. Wounds and controls were harvested 72 hours post-injury. Collagen fibers have been stained with Sirius red and appear white. Red open arrows indicate hair follicles. A. Unwounded skin from an E19 fetus (200×) for comparison with the E16 wounds. B. Normally, E16 fetal wounds heal scarlessly (200×). The dermal collagen fibers are thin, and their reticular arrangement is indistinguishable from the organization of collagen in unwounded skin. C. In contrast, the collagen fibers in anti-FM antibody-treated E16 fetal wounds are thicker and more randomly arranged (400×). D. Collagen fibers are thinner and have a reticular arrangement in the E16 wounds treated with IgG control solution (400×). E. Unwounded skin from an E21 fetus for comparison with the E18 wounds—400× (left) and 1000□× (right). F. Usually, E18 fetal wounds heal with scar. No hair follicles are seen in the scar (400× (left)). Collagen fibers in the area of scar are thicker and are arranged randomly with greater distances between fibers, which is better seen at higher magnification (1000× (right)). G. Addition of FM to E18 wounds, however, inhibits scarring—400× (left) and 1000× (right). Here the collagen fibers are thin, while the organization of collagen in the wound bed is very similar to the architecture of unwounded E21 skin. H. Wounds treated with collagen control solution have thicker, randomly arranged fibers with greater inter-fiber distances—400× (left) and 1000× (right).

Figure 10:
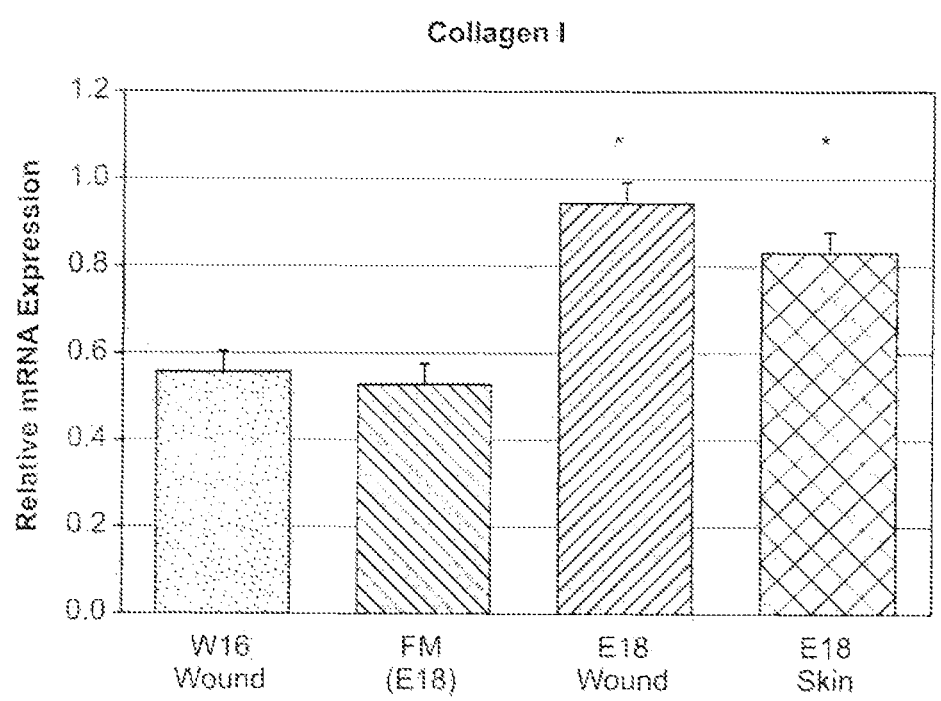

FIG. 10 shows relative mRNA expression of type I collagen in FM-treated (E18) wounds compared with scarless (E16) wounds, scarring (E18) wounds, and unwounded skin (E18). Consistent with results FIG. 5, FM treated wounds with exhibited less ECM deposition as exemplified by gene expression for type I collagen. RNA was isolated from fetal tissue 12 hours post-wounding and reduced-cycle, RT-PCR was performed. Relative mean mRNA expression is depicted ±SEM. Student's t test was used to perform pairwise comparisons of means. P values <0.05 were considered significant. Asterisks indicate significant differences between control wound/skin and the FM-treated group.

Figure 11:
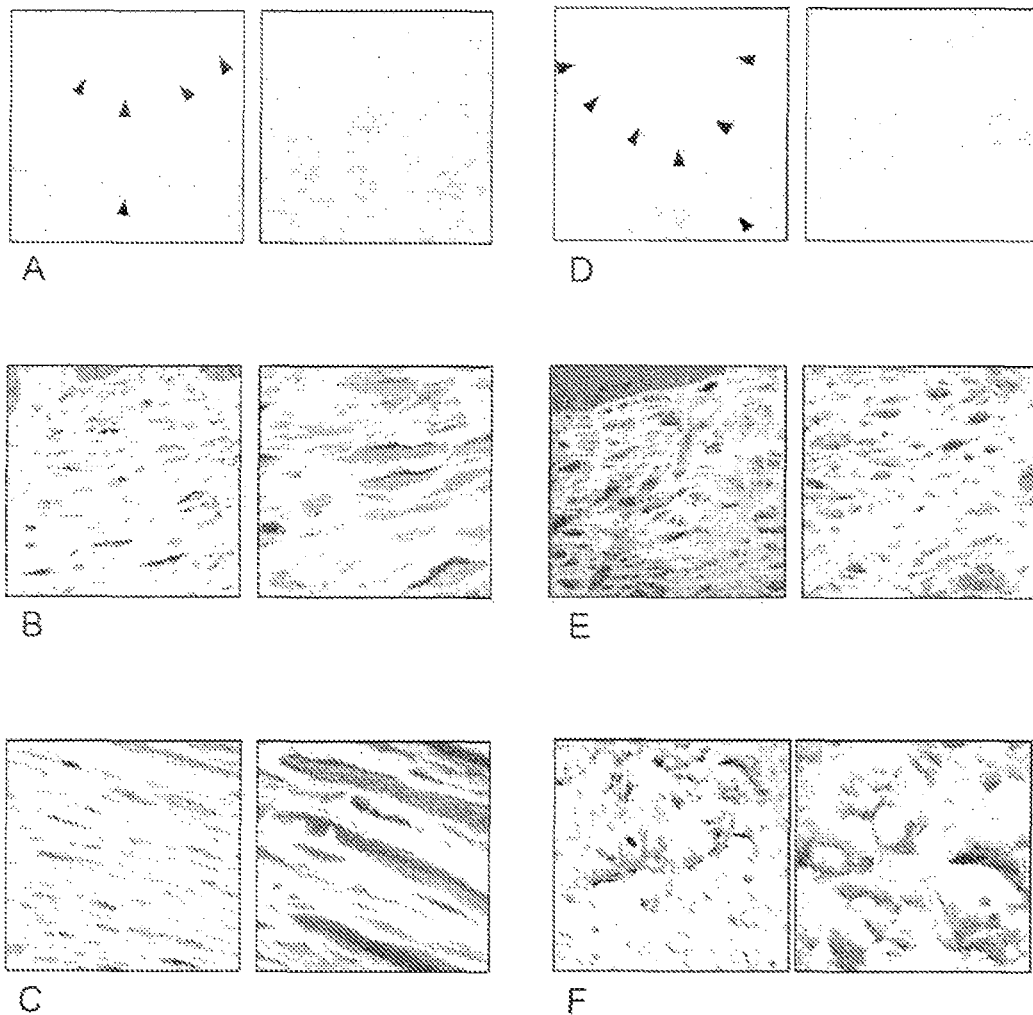

FIG. 11 shows adult wounds treated with FM (0.4 mg/ml) or PBS control solutions with significant improvement in collagen architecture and increased dermal tissue regeneration. Wounds were harvested 2 weeks post-injury, and tissue sections were stained with either H&E or Sirius red (for confocal microscopy). Black arrows mark the wound bed, and red arrows indicate permanent dye and disruption of the panniculus carnosus muscle. A. H&E staining of an adult wound treated with FM—200× (left) and 400× (right) magnification. At higher magnification, dermal collagen fibers appear to have a parallel arrangement. B. Confocal microscopy of the superficial dermis (near the epidermal-dermal border) of a FM-treated adult wound—400× (left) and 1000× (right) magnification. The white collagen fibers have a relatively uniform, linear appearance and lie parallel to the overlying epidermis. C. Confocal microscopy of the deep dermis of a FM-treated adult wound—400× (left) and 1000× (right) magnification. Again, parallel organization of collagen fibers is seen. D. H&E staining of an adult wound treated with control PBS solution—200× (left) and 400◻× (right) magnification. The wound area is larger than in the FM-treated wounds. E. Confocal microscopy of the superficial dermis of a control adult wound illustrating the random deposition of collagen fibers—400× (left) and 1000× (right) magnification. F. Confocal microscopy of the deep dermis of a control adult wound—400× (left) and 1000× (right) magnification. Here the disorderly pattern of collagen deposition and great variation in collagen fiber morphology is more clearly seen.

DETAILED DESCRIPTION

I. Definitions

The term "topical application," as used herein, means to apply or spread the compositions of the present invention onto the surface of the skin.

The term "dermatologically-acceptable," as used herein, means that the compositions or components thereof so described are suitable for use in contact with human skin without undue toxicity, incompatibility, instability, allergic response, and the like.

The term "safe and effective amount" as used herein means an amount of a compound or composition sufficient to significantly induce a positive benefit, preferably a positive skin appearance or feel benefit, including independently the benefits disclosed herein, but low enough to avoid serious side effects, i.e., to provide a reasonable benefit to risk ratio, within the scope of sound judgment of the skilled artisan.

The term "FM" as used herein means not only FM, but also any functionally equivalent molecule with or without genetic modification.

The term "wild-type FM protein" as used herein means non-genetically modified, naturally occurring FM present in tissues.

The term "recombinant FM cDNA" as used herein means FM cDNA (either genetically modified or not) that has been cloned into a suitable expression vector (e.g., plasmid, adenovirus).

The term "genetically modified" refers to modification of the DNA expressing a protein such as FM so as to increase a property of the protein, e.g., transcription efficiency, purification efficiency, biological activity by increasing binding efficiency, resistance to proteolysis, etc.

The term "recombinantly expressed" as used herein means fetal tissue derived cDNA (either genetically modified or not) that has been cloned into a suitable expression vector (e.g., plasmid, adenovirus) for purposes of obtaining protein expression from the cDNA.

The term "lysates" as used herein means compositions obtained through lysing cells using a suitable detergent.

The term "extracts" as used herein means compositions obtained after further purification or concentration of cell lysate material.

The term "media" as used herein means compositions isolated from the external environment of unmodified or genetically modified fetal cells or tissues.

The term "compounds" as used herein may be considered equivalent to "molecules", although the term "molecules" is more preferable when describing a single entity.

"Healthy skin" or "normal skin" refers to non-lesional skin, i.e., with no visually obvious erythema, edema, hyper-, hypo-, or uneven pigmentations, scale formation, xerosis, or blister formation. Histologically, healthy or normal skin refers to skin tissue with a morphological appearance comprising well-organized basal, spinous, and granular layers, and a coherent multi-layered stratum corneum. In addition, the normal or healthy epidermis comprises a terminally differentiated, stratified squamous epithelium with an undulating junction with the underlying dermal tissue. Normal or healthy skin further contains no signs of fluid retention, cellular infiltration, hyper- or hypoproliferation of any cell types, mast cell degranulation, parakeratoses, etc., and implies normal dendritic processes for Langerhans cells and dermal dendrocytes. This appearance is documented in dermatological textbooks, for example, *Histopathology of the Skin*, Lever and Schaumburg-Lever (eds.), J. B. Lippincott Company (1991) and *Textbook of Dermatology*, Champion et al., (eds.), 5th Ed. Blackwell Scientific Publications (1992), especially Chapter 3 "Anatomy and Organization of Human Skin"; *Physiology, Biochemistry and Molecular Biology of the Skin, Vols. I And II*, Goldsmith (ed.), Oxford Press (1991), the full disclosures of which are expressly and completely incorporated herein by reference.

The term "promoting skin condition" includes prophylactically promoting and/or therapeutically promoting skin condition, including visible and/or tactile discontinuities in skin. As used herein, prophylactically promoting skin condition includes delaying, minimizing and/or preventing visible and/or tactile discontinuities in skin. As used herein, therapeutically promoting skin condition includes ameliorating (e.g., diminishing, minimizing and/or effacing, discontinuities in skin). Promoting skin condition involves improving skin appearance and/or feel.

II. Skin Conditions

A. Skin Inflammation

Skin inflammation as used herein generally includes non-allergic skin inflammatory condition, allergic skin inflammatory condition, neurogenic skin inflammatory condition, TNF-alpha mediated conditions, UV radiation (UVR) induced skin inflammatory conditions, and miscellaneous skin inflammatory conditions.

"Non-allergic skin inflammatory condition" refers to an inflammatory condition of the skin which is not solely mediated by a specific antigen. Such conditions include, e.g., irritant contact dermatitis, psoriasis, eczema, pruritus, seborrheic dermatitis, nummular dermatitis, lichen planus, acne vulgaris, comedones, polymorphs, nodulocystic acne, conglobata, senile acne, secondary acne such as solar acne, medicinal acne or professional acne; other types of keratinization disorders, for example, ichthyoses, ichthyosiform conditions, Darier malady, palmoplantary keratodermies, leucoplasies and leucoplasiform conditions and lichen; other dermatologic disorders such as blistery dermatoses and collagen maladies; and extrinsic aging of the skin, be it photoinduced or not.

"Allergic skin inflammatory condition" refers to skin inflammation caused by one or more allergen. "Allergen" refers herein to a substance which induces symptoms of immediate hypersensitivity by inducing IgE antibody responses and delayed hypersensitivity reaction. Generally, such responses require a sensitization of the immune system to the allergen. For instance, mosquito bite-induced itch and inflammation is thought to result from an IgE and IgG mediated allergic reaction to antigenic materials in mosquito salivary glands. The primary target in immediate allergic reactions are mast cells, which have high affinity IgE receptors (Ohtsuka E, et al., *Jpn J Pharmacol* 86:97-105, 2001). Upon IgE-dependent stimulation, mast cells release several pro-inflammatory mediators such as TNF-alpha, Kulka M and Befus A D., *Arch Immunol Ther Exp* (Warsz) 51:111-110, 2003). TNF-alpha is found pre-formed and stored in granules of mast cells or newly synthesized following mast cell activation (Iuvone T, et al., *Br J Pharmacol.* 128:700-704, 1999). TNF-alpha is a multifunctional cytokine and a key mediator of immune and inflammatory response and it has been found pre-formed and stored in granules of mast cells or newly synthesized following mast cell activation (Gordon J R, and Galli S J., *Nature.* 346:274-276, 1990)

"Neurogenic skin inflammatory condition" refers to an inflammatory condition of skin related to proinflammatory neuropeptide release (e.g., during times of emotional or psychological stress) that may occur concomitant with or separate from non-allergenic or allergenic inflammatory skin conditions. For instance, stress induced acne has been proposed as an example of neurogenic inflammation. The skin is innervated by primary afferent sensory nerves, postganglionic cholinergic parasympathetic nerves, and postganglionic adrenergic and cholinergic sympathetic nerves. Sensory nerves are derived from the dorsal root ganglion and are present in all parts of the skin representing the initial somatic portion of the afferent sensory pathway. The cutaneous sensory nervous system comprises a network of fine C fibers within the skin that innervate multiple cell types and play an important role in inflammation. The epidermis is also innervated by a three-dimensional network of unmyelinated nerve fibers with free branching endings that arise in the dermis. Sensory nerves not only function as an afferent system to conduct stimuli from the skin to the central nervous system, but they also act in an efferent neurosecretory fashion to stimulate target tissues through their terminals. Various stimuli, such as noxious stimuli, may directly activate the peripheral endings of primary sensory neurons generating impulses that are conveyed centrally as well as, through antidromic axon-reflexes, peripherally. Upon release of neuropeptides from sensory terminals, important visceromotor inflammation and trophic effects occur in the peripheral tissues. Normal human skin expresses a variety of neuropeptides that are either directly derived from sensory neurons or from skin cells such as keratinocytes, microvascular endothelial cells or fibroblasts. In addition, immune cells that either constitutively reside in the skin, such as mast cells, or that infiltrate the skin during inflammation have been reported to produce neuropeptides. Cutaneous nerve fibers can modulate inflammatory reactions through the local release of neuropeptides, which are able to regulate both acute and chronic aspects of cutaneous inflammatory processes, such as vascular motility, cellular trafficking, activation and trophism. Clinical evidence in support of a connection between neuropeptides secretion and the development of inflammation is found in various skin diseases, such as atopic dermatitis, psoriasis and alopecia areata, and acne which are commonly exacerbated during periods of emotional stress. Indeed, stress has been shown to elicit the release of substance P, a potent proinflammatory neuropeptide (Reviewed in Toyoda M, et al., Neuropeptides and sebaceous glands. *Eur J Dermatol* 12:422-427, 2002). Several studies have demonstrated that mast cells are often found in close contact with nerves and that there may be functional interactions between MCs and the nervous system. In addition, recent evidence suggests that substance P is an important mediator in intimate nerve-mast cell cross talk. These findings suggest that substance P endogenously released by dermal nerve fibers may be important in the regulation of endothelial-leukocyte interaction via mast cells. It has been demonstrated that the proinflammatory effects induced by mast cell degranulation products is inhibited by a blocking antiserum to TNF-alpha. Thus, a cascade of cellular events involving mast cell degranulation and the release of proinflammatory cytokines such as TNF-alpha will then induce adhesion molecules such as E-selectin on the adjacent venular endothelium that would then facilitate the local accumulation of blood leukocytes and further augment the inflammatory response. Thus, TNF-alpha may also modulate neurogenic inflammation.

"TNF-alpha mediated conditions" refers to local skin disorders where TNF-alpha is a primary mediator leading to the manifestation of the disorders. TNF-alpha, previously known as cachectin, is produced by a large number of cells or tissues including neutrophils, activated lymphocytes, macrophages, NK cells, LAK cells, astrocytes, endothelial cells, smooth muscle cells, mast cells, keratinocytes and other epithelial cell types. This particular cytokine governs a wide variety of biological activities including: cytotoxic effects against tumors, activation of neutrophils, normal proliferation of cells, inflammatory, immunological, and antiviral responses. A membrane-bound form of TNF-alpha has been located in lymphocytes or monocytes where it is involved in intracellular signaling and activation. The specific overproduction of TNF-alpha is known to be an important determinant for a number of diseases, infections, and inflammatory conditions including rheumatoid arthritis, cachexia, endotoxin shock, inflammatory bowel disease, Crohn's disease, psoriasis, contact dermatitis, adult respiratory distress syndrome, infections, transplantation, ischemic/reperfusion damage, diseases involving eosinophils (e.g. asthma, allergy, etc.), graft-versus-host reactions, bone resorption, inflammatory bowel disease, multiple sclerosis (MS), diabetes, AIDS and Alzheimer's disease and/or the weight loss associated with Alzheimer patients (Reviewed in Beutler B., *Tumor Necrosis Factors, The Molecules And Their Emerging Role In Medicine* Raven Press, 1992, and European Cytokine Network, 5(2) (1994).

"UVR mediated skin inflammatory condition" refers to an inflammatory condition of skin from excessive UVR exposure.

"Miscellaneous skin inflammatory condition" refers to an inflammatory condition of skin not otherwise specified above affecting intact or non-intact skin. Skin infections are examples of inflammatory skin conditions occurring in intact skin or non-intact skin. Wounds are examples of inflammatory skin conditions occurring in non-intact skin.

As noted above, the largest organ in the body, the skin, also makes TNF-alpha. Since skin represents the border to a hostile environment, it needs an arsenal of biological weapons to combat such insults as chemical irritants, bacteria, insect bites, sunlight and physical trauma. Pro-inflammatory cytokines stand as ready messengers to inform and direct the immune system upon challenge.

B. Skin Pigmentation

The difference in skin color between different individuals and races are determined by the amount and distribution of melanin produced by melanocytes. In fact, differences in skin shade and color are determined not by the number and density of the melanocytes, which are basically identical in all humans of any race, but by their degree of melanogenic activity, the number and size of the melanosomes, the type of melanin deposited onto melanosomes, and the donation of mature melanosomes to surrounding keratinocytes. (Reviewed in Abdel-Malek Z., *The Pigmentary System: Physiology and Pathophysiology*. Eds. Nordlun J J, et al., pp. 115-122, 1998).

Regulation of Skin Pigmentation

Melanin production and cell proliferation by melanocytes is regulated by several factors including ultraviolet radiation (UVR), steroid hormones, inflammatory mediators, growth factors, peptide hormones, and melanotropins (Reviewed in Abdel-Malek Z, 1998). Exposure to UVR stimulates the synthesis of a variety of hormones, cytokines, and growth factors by epidermal cells or keratinocytes. Keratinocytes exposed to UVR produce interleukin (IL)-1 and tumor necrosis factor (TNF)-alpha, two major inflammatory cytokines. Moreover, TNF-alpha has been shown to play an important role in the formation of sunburn (i.e., apoptotic) keratinocytes. The synthesis of basic fibroblast growth factor (bFGF) by keratinocytes was also enhanced by UVR treatment. Basic FGF is mitogenic for human melanocytes. In addition, UVR may also increase keratinocyte endothelin (ET)-1,-melanocyte stimulating hormone ($\square$MSH, and adrenocorticotropic hormone (ACTH) synthesis. ET-1 is a potent mitogen and melanogen for melanocytes that is regulated by IL-1, TNF-alpha, or UVR, while MSH and ACTH which are mitogenic and melanogenic may function as transducers for the melanogenic effects of UVR. ET-1 may also act synergistically with bFGF and $\square$MSH to stimulate melanocyte proliferation.

The effects of sex steroid hormones (androgens and estrogens) on cutaneous pigmentation have been recognized for a along time. The increased pigmentation of the areola and genitalia has been attributed mostly to these hormones. Changes in the levels of the female sex hormones during pregnancy have been implicated in the skin darkening, seen in melasma (Abdel-Malek Z, 1998).

The clinical observation of post-inflammatory hyperpigmentation has also implicated immune inflammatory mediators in this phenomenon. Inflammatory cytokines such as IL-1 and TNF-alpha increase production and secretion of endothelins by keratinocytes (Manaka L, et al., *Br J Dermatol* 145:895-903, 2001). Other inflammatory mediators of the cyclooxygenase pathway such as prostaglandin E have been found to increase in skin following UV exposure and to increase melanogenesis (Abdel-Malek Z, 1998).

Although many molecules are involved in regulation of melanogenesis, it is clear from the preceding section that the inflammatory cytokine TNF-alpha plays a major role as an initial mediator in the regulation of skin pigmentation upon exposure to UVR and upon other conditions that may induce or increase skin inflammation such as injury, acne, insect bites, etc. TNF-upregulation may then induce the expression of other molecules that may further increase the inflammatory and/or melanogenetic stimuli. For instance, TNF-alpha stimulates inflammatory mediator prostaglandin E2 production by human synovial cells and dermal fibroblasts (Dayer, J M, et al., *J Exp Med.* 162:2163-2168, 1985) as well as melanogenetic mediator endothelin 1. Thus, the inhibition of TNF-alpha activity may be useful in preventing an entire cascade of inflammatory and melanogenetic stimuli that can result in undesirable effects on skin pigmentation.

In addition, the regulation of bFGF may also have important implications for skin color. Basic FGF which is induced by UVR and is mitogenic for melanocytes also enhances stem cell factor (SCF) production (Sugimoto Y, et al., *J Cell Physiol.* 181:285-294, 1999). SCF induces melanocytic hyperplasia with increased melanocyte number and increased melanin (Grichnik J M, et al., *J Am Acad Dermatol.* 33:577-583, 1995). Overexpression of SCF in the skin and serum of systemic sclerosis patients is associated with hyperpigmentation (Kihira C, et al., *J Dermatol Sci.* 20:72-78, 1998 and Yamamoto T. et al., *Br J Dermatol.* 144:199-200, 2001). Thus, modulation of bFGF may not only affect bFGF, but SCF effects on melanocyte proliferation and melanin production as well.

C. Dermal Collagen—Organization

Dermal Components

The dermal layer provides the support and blood supply for the epidermis. The dermal layer is also important in maintaining the elasticity, thickness, and appearance of the skin. The dermis is largely comprised of fibroblast cells and ECM. Immune cells such as mast cells, polymorphonuclear leukocytes, lymphocytes, and macrophages are also present in the dermis. The composition of the ECM is largely determined by fibroblasts that elaborate various components such as collagens, elastins, and other matrix proteins. The ECM acts as a scaffold for cell adhesion, proliferation, migration, and differentiation and gives mechanical strength and elasticity to tissue (Kuwaba K, et al., *J Dermatol Sci.* 29:185-194, 2002). The major component of ECM is collagen whose functions will be further detailed in the next section. Closely associated with dermal collagen are elastin fibers which are found at the periphery of collagen bundles and endow the skin with recoil properties (i.e., the skin's ability to "spring back" after being stretched). It is believed that damage to the elastin fibers leads to the decreased skin elasticity seen in aged skin. Other matrix proteins include glycoproteins such as fibronectin and tenascin which influence cell migration, adhesion, and orientation, glycosaminoglycans (GAGs) such as hyaluronic acid, dermatan sulfate, and heparin sulfate which may be important for cell growth, membrane receptor function, and adhesion, and proteoglycans such as decorin (Baumann L. Basic science of the dermis. *Cosmetic Dermatology Principles and Practice*. Hong Kong: The McGraw Hill Companies, Inc., pp. 9-12, 2002). GAGs and proteoglycans have been shown to be key regulators of a variety of cellular behaviors and will be discussed further below.

Dermal Collagens—General Characteristics

Collagens comprise the most abundant proteins in the ECM. Collagens are the major structural element of all connective tissues where they contribute to the stability and structural integrity of tissues. Over 21 different collagens have been described. Based on their structure and supramolecular organization, they have been divided into fibril-forming collagens (types I, II, III, V, and XI), basement membrane collagen (type IV), microfibrillar collagen (type VI), anchor fibrils (type VII), hexagonal network-forming collagens (types VIII and X), fibril-associated collagens (types IX, XII, XIV, XIX, XX, and XXI), transmembrane collagens (types XIII and XVII), and multiplexins (types XV, XVI, and XVIII). Despite their high structural diversity, all members of the collagen family have a characteristic right-handed triple helix composed of three □-chains. About 90% of total collagens are fibril-forming collagens. (Reviewed in Gelse K, Poschl E, and Aigner T. Collagens-structure, function, and biosynthesis. *Adv Drug Del Rev* 55, 1531-1546, 2003). Type I collagen comprises 80-85% of the dermal matrix and is responsible for the tensile strength of the dermis. Type I collagen is decreased in photoaged skin and increased in skin after dermal injury (e.g., trauma, dermabrasion). Type III collagen is the second most abundant dermal collagen, comprising 10-15% of the dermal matrix and is important for skin compliance (Baumann L. Basic science of the dermis. *Cosmetic Dermatology: Principles and Practice*. Hong Kong: The McGraw Hill Companies, Inc., pp. 9-12, 2002).

Dermal Collagen—Organization

Because the major component of ECM is collagen, the mechanical, physiological, and biological properties of ECM are affected by the supra-molecular structure of collagen such as the organization of collagen molecules into fibrils, of fibrils into bundles, and of bundles into a tissue-specific matrix, the structure or organization of collagen can profoundly impact the function or appearance of various tissues (Kuwaba et al., 2002). Innate mutations in the collagen molecule or molecules involved in collagen fibrillogenesis can lead to collagen disorganization and disease entities such as Ehlers Danlos (Ameye L, and Young M F. Mice deficient in small leucine-rich proteoglycans: novel in vivo models for osteoporosis, osteoarthritis, Ehlers-Danlos syndrome, muscular dystrophy, and corneal diseases. *Glycobiology*. 12: 107R-116R, 2002). Acquired conditions such as prolonged exposure to UVR can also lead to destruction of normal tissue architecture and replacement by disorganized collagen with thinning and wrinkling of the skin. Lastly, acquired injury or disease to the normal collagen architecture of various tissues can lead to the production and deposition of disorganized collagen during the repair process. Examples of this include hepatic cirrhosis, pulmonary fibrosis, and dermal scar formation. Thus, many disparate processes, with or without over skin injury, can lead to collagen disorganization and the promotion of collagen organization can potentially be used to treat many different clinical conditions.

Glycosaminoglycans

GAGs constitute a considerable fraction of the glycoconjugates found on cellular membranes and in the ECM of virtually all mammalian tissues. Their ability to bind and alter protein-protein interactions or enzymatic activity makes them important determinants of cellular responsiveness in development, homeostasis, and disease. Although heparin sulfate, heparin, and hyaluronic acid have been more commonly studied, dermatan sulfate is the predominant GAG expressed in skin accounting for as much as 0.3% dry weight of skin. In addition, dermatan sulfate, also known as chondroitin sulfate B, has been shown to promote bFGF and FGF-7 activity. Dermatan sulfate and dermatan sulfate associated proteoglycans such as decorin are markedly up-regulated after injury. Dermatan sulfate derived from wounds activates endothelial leukocyte adhesion through stimulation of ICAM-1. Indirectly, the production of dermatan sulfate proteoglycans such as decorin and biglycan have been associated with increased scarring (Reviewed in Trowbridge J M, and Gallo R L. Dermatan sulfate: new functions from an old GAG. *Glycobiology*. 12:117 R-125R, 2002; Trowbridge J M, et al., *J Biol Chem*. 277:42815-42820, 2002). Thus, dermatan sulfate is associated with increased leukocytosis which can contribute to inflammation as well as increased bFGF which can contribute to melanocyte proliferation. In addition, treatment with chondroitinase B, a lyase that degrades dermatan sulfate as its sole substrate, inhibited bFGF mediated fibroblast proliferation (Denholm E M, et al., *Eur J Pharmacol*. 400:145-153, 2000; Pojasek K, et al., *J Biol Chem*. 277:31179-31186, 2002). Therefore, modulation of GAG levels, either directly through degradation with enzymes or indirectly through modulation of their associated proteoglycans can potentially minimize inflammation and hyperpigmentation. Though not wishing to be bound by a particular theory, the chondroitinase B mediated decrease in dermatan sulfate levels may decrease bFGF mediated effects on fibroblast and melanocyte proliferation with resultant promotion of skin regeneration, collagen organization, decreased hyperpigmentation, as well as decrease ICAM-1 mediated effects with resultant inhibition of leukocytosis and inflammation.

In addition, there is evidence suggesting that the size of GAGs such as dermatan sulfate change during repair processes and that the size of a particular GAG can have potential implications for collagen organization. Specifically, while small leucine rich proteoglycans (SLRPs) are known to impact formation of collagen fibrils, the size of particular GAGs on SLRPs can potentially impact the spacing of the collagen fibrils (i.e., interfibrillar distance) as will as the diameter of collagen fibrils. For example, elongated GAGs were associated with enlarged interfibrillar spaces with thin collagen fibrils, while normal sized GAGs were associated with tightly packed, thick collagen bundles during repair in adult mice (Kuwaba K, et al., *J Dermatol Sci*. 29:185-194, 2002). Thus modulation of GAG length through various enzymes specific for a particular GAG can be used to further promote collagen organization. For example, keratan sulfates (another type of GAG) can be modulated through use of various keratan sulfate degrading enzymes (Reviewed in Yamagishi K, et al., *J Biol Chem*. 278:25766-25772, 2003).

Small Leucine-Rich Proteoglycans

Another important class of matrix proteins are SLRPs that have been shown to bind to transforming growth factor-beta (TGF-beta) and to regulate collagen fibrillogenesis. Decorin and biglycan are two members of the SLRP family that have already been discussed above. The SLRP family is rapidly growing and includes at least 13 members (Reviewed in Ameye L and Young M F. Mice deficient in small leucine-rich proteoglycans: novel in vivo models for osteoporosis, osteoarthritis, Ehlers-Danlos syndrome, muscular dystrophy, and corneal diseases. *Glycobiology* 12:107 R-116R, 2002). Most SLRPs can be grouped into three classes. Decorin and biglycan are representative of class I SLRPs in that they contain a unique N-terminal cysteine sequence and carry one and two chondroitin or dermatan sulfate chains, respectively. Unlike class I, class II SLRPs contain a different N-terminal cysteine sequence and generally carry polylactosamine or keratan sulfate chains. FM, lumican, keratocan, and osteoadherin are examples of class II SLRPs.

Class III SLRPs exhibit a characteristic N-terminal cysteine sequence and contain sulfated tyrosine residues in the N-terminal end.

In general, class I SLRPs tends to be more ubiquitous than class II members with the distribution of class II SLRPs being the most tissue specific. Several SLRPs bind to collagens type I, II, V, VI, XII, and XIV to modulate collagen fibrillogenesis. In addition, at least three SLRPs (decorin, biglycan, and FM) bind to TGF-beta, a multifunctional cytokine involved in inflammation apoptosis, cell proliferation, differentiation, and scar formation. Based on these findings, several patents have been filed concerning the ability to reduce scar tissue or wound contraction by neutralizing TGF-beta activity through the application of potential TGF-beta modulators within the decorin proteoglycan family, including decorin, biglycan and FM (U.S. Pat. Nos. 6,509,314; 5,583,103; 5,958,411; 5,654,270; and 5,824,655).

In addition, because decorin production by fibroblasts appears to diminish with age and photo damage, and because lack of decorin in skin is associated with decreased tensile strength and skin fragility, several patents exist that specifically mention decorin, but not other SLRPs, in the context of preventing or treating skin aging. For instance boosting decorin synthesis in skin by topical application of conjugated linoleic acid, petroselinic acid, and other compounds (U.S. Pat. Nos. 6,551,602; 6,455,057; 6,440,434; 6,423,325; 6,287,553; 6,042,841) or actual use of decorin in cosmetic or dermatologic compositions (U.S. publication No. 20030124152).

Existing knockout mice models demonstrate that although SLRPs belong loosely to the same proteoglycan family, they have distinctly different effects that are not interchangeable. For instance, decorin (class I SLRP) deficient mice demonstrate skin fragility, while FM (class II SLRP) deficient mice demonstrate no known skin defects (Ameye L and Young M, 2002, Glycobiology, 12(9): 107R-116R). Furthermore, targeted disruption of biglycan (class I SLRP) results in diminished bone mass and no described skin abnormalities, while lumican (class II SLRP) knockout mice demonstrate corneal opacity. Thus, although decorin, biglycan, FM, and lumican belong to the same SLRP family with decorin/biglycan and FM/lumican belonging to the same class of proteoglycans, each member has distinct biological functions with different effects on collagen fibrillogenesis, structure, and organization that are not interchangeable.

In terms of tissue distribution, decorin and biglycan are ubiquitous, although they show a quite divergent localization within tissues, with decorin found more in the ECM of tissues where it is bound to type I collagen (Vogel K G, et al., *Biochem J*. 223:587-597, 1984) and biglycan localized more closely around cells (Bianco P, et al., *J Histochem Cytochem*. 38:1549-1563, 1990). Decorin is the dominant dermatan sulfate proteoglycan distributed on the surface of collagen fibrils in skin (Kuwaba K, et al., *J Dermatol Sci*. 29:185-194, 2002). FM has a somewhat more restricted distribution with high concentrations in cartilage, tendon and sclera, while low in skin and mineralized bone (Heinegard D, et al., *J Biol Chem*. 261:13866-13872, 1986). Lumican is found mainly in the cornea (Reviewed in Ameye and Young, 2002).

D. Aging

With increasing age, there is decreased ability of fibroblasts to proliferate and to synthesis collagen and other ECM proteins such as proteoglycans (Takeda K, et al., *J Cell Physiol*. 153:450-459, 1992). For instance, type I collagen and decorin production is decreased in aged skin (Hunzelmann N, et al., *Biochim Biophys Acta*. 1360:64-70, 1997 and Carrino D A, et al., *J Biol Chem*. 278:17566-17572, 2003). In addition, older fibroblasts also exhibit higher basal and induced steady-state mRNA levels of interstitial collagenase (Burke E M, et al., *Exp Gerontol*. 29:37-53, 1994). Thus, the relative balance between ongoing ECM deposition (e.g., type I collagen, decorin) and degradation (e.g., collagenase) is tilted towards overall ECM degradation with age. This lead to progressive thinning and disruption of the supporting dermis that then results in sagging and consequent furrowing of the epidermis, i.e., the formation of wrinkles. On a microscopic level, the collagen in aged skin is characterized by thickened fibrils organized in rope-like bundles, which are in disarray as compared to the organized pattern seen in younger skin (See, for example, Oikarinen A., *Photodermatol Photoimmunol Photomed* 7: 3-4, 1990).

Besides chronoaging, accelerated skin aging as a result of sun and/or environmental contaminants exposure can also occur. For example, photoaging occurs as a result of UVR exposure. UVR exposure initiates an inflammatory reaction in skin that is mediated in large part by TNF-alpha as well as other factors discussed herein. TNF-alpha has been shown to inhibit collagen and fibronectin synthesis in dermal fibroblasts (Mauviel A, et al, *J Invest Dermatol*. 96:243-249, 1991; Mauviel A, et al., *FEBS Lett*. 236:47-52, 1988) as well as promote collagen degradation (Dayer J M, et al., *J Exp Med*. 162:2163-2168, 1985; Siwik D A, et al., *Circ Res*. 86:1259-1265, 2000)—both of which contribute to skin aging. UVR exposure dramatically up-regulates the production of several types of collagen degrading enzymes known as matrix metalloproteinases (MMPs) (interstitial collagenase also belongs within this category of enzymes). Because MMPs degrades collagen, long-term elevations in MMPs as a result of UVR exposure likely results in the disorganized and clumped collagen seen in photoaged skin. Thus MMPs may represent a mechanism by which collagen type I levels are reduced following UV exposure (Baumann L. Photoaging. *Cosmetic Dermatology: Principles and Practice*. Hong Kong The McGraw Hill Companies, Inc., pp. 13-20, 2002). Significant levels of UVR also lead to degradation of the dermis. Furthermore, UVR also induces bFGF, which among other effects, is known to stimulate plasminogen activator and collagenase activity that facilitate ECM breakdown (Reviewed in Abraham J A and Klagsbrun M. Modulation of wound repair of members of the fibroblast growth factor family. Ed. Clark RAF. *The Molecular And Cellular Biology Of Wound Repair*. Vol. xxiii. New York: Plenum Press, pp. 195-248, 1996) modulation of bFGF activity by FM may also prevent or minimize the effects of photoaging including collagen disorganization.

Thus, both normal and accelerated aging is associated with an overall decrease in ECM production (e.g., collagen, decorin, fibronectin) and an increase in ECM degradation (e.g., MMPs and plasminogen activator) that leads to progressive ECM thinning and collagen disorganization and clumping. Therefore methods to prevent decreased ECM production or increased ECM degradation (e.g., by inhibition of TNF-alpha and/or bFGF) or methods to promote collagen organization can be useful in promoting the condition of skin, especially of aged skin.

III. Methods and Compositions for Promoting Skin Regeneration

In one aspect of the present invention, described herein is a method for modulating skin conditions such as promoting skin regeneration. The method comprising a step which can be promoting collagen organization, modulating skin inflammatory conditions, modulating skin pigmentation, and combinations thereof.

In one embodiment, the method of modulating skin conditions can be achieved by, for example, modulating the level of a compound which can be SLRPs, GAGs, MMPs or combinations thereof in skin of a mammal. The SLRPs can be, for example, FM, lumican, decorin, biglycan, and combinations thereof, the GAGs can be, for example, dermatan sulfate, chondroitin sulfate, keratan sulfate, and combinations thereof, and the MMPs can be, for example, MMP-1 or MMP-9, or combinations thereof. The level of SLRPs can be modulated by applying to the skin a composition comprising an effective amount of one or more of the SLRPs. The skin can be intact or non-intact with or without a dermal injury or non-intact skin with epidermal injury. The level of the dermatan sulfate, chondroitin sulfate, keratan sulfate, and combinations can be modulated, for example, by applying to the skin a composition comprising one or more enzymes that modulate collagen fibrillogenesis and interfibrillar spacing and/or enzymes that modulate unorganized matrix deposition by fibroblasts. Exemplary enzymes that modulate collagen fibrillogenesis, interfibrillar spacing, and/or unorganized matrix deposition by fibroblasts include, but are not limited to, chondroitinase AC, chondroitinase B, endo-beta-galactosidases, keratanase, keratanase II, Bc keratanase II, and combinations thereof. The level of MMPs can be modulated by applying to the skin a composition comprising an effective amount of one or more of the MMPs to modulate collagen degradation.

In another embodiment, the method of modulating skin conditions can be achieved by modulating skin inflammatory conditions or modulating skin pigmentation. The skin inflammatory conditions can be, for example, non-allergic skin inflammatory conditions, allergic skin inflammatory conditions, neurogenic skin inflammatory conditions, UVR induced skin inflammatory conditions, miscellaneous skin inflammatory conditions, and combinations thereof. The skin inflammatory conditions and/or skin pigmentation can be achieved by, for example, the modulation of the level of FM, lumican, decorin, and/or biglycan, which may modulate TNF-alpha activity, or modulation of the level of dermatan sulfate, which may modulate leukocytosis in the skin. The level of dermatan sulfate can be modulated by one or more enzyme, for example, chondroitinase B. The skin pigmentation may also be achieved via modulation of the level of dermatan sulfate, which modulates bFGF activity. Basic FGF activity can then in turn directly modulate melanocyte proliferation or indirectly by enhancing production of SCF. SCF can directly modulate melanocyte proliferation and melanin production. Alternatively, skin pigmentation can be modulated by modulating the level of dermatan sulfate, chondroitin sulfate, keratan sulfate, and combinations thereof by applying to the skin a composition comprising one or more enzymes such as chondroitinase AC, chondroitinase B, endo-beta-galactosidases, keratanase, keratanase II, Bc keratanase II, and combinations thereof.

In another aspect of the present invention, it is disclosed herein compositions comprising one or more compounds expressed by fetal tissues which are effective for promoting skin regeneration and methods of using the compositions. In particular, the present invention provides a composition that improves, minimizes, prevents, and or treats visible and/or tactile discontinuities in skin. Such discontinuities may be induced or caused by internal and/or external factors, and include the signs of skin aging described herein. Promoting skin condition is understood to include, but not be limited to:

1) treatments that improves, minimizes, prevents, and or treats skin aging as manifested by wrinkling, sagging, uneven pigmentation, loss of elasticity or resiliency; 2) treatments that result in smoother, softer skin texture or appearance; 3) treatments that improves, minimizes, prevents, and or treats skin inflammation; 4) treatments that improves, minimizes, prevents, and or treats hyperpigmentation or uneven skin pigmentation from causes not related to skin aging (e.g., acne, insect bites, etc); 5) treatments that promote ECM organization; and 6) treatments that promote skin regeneration.

In still another aspect of the present invention, methods are provided for promoting the condition of skin utilizing SLRPs, which among others includes FM, lumican, decorin, and biglycan as well as utilizing enzymes to modulate GAGs associated with proteoglycans. In one embodiment, the present invention includes skin regeneration and dermal collagen organization as well as methods to prevent or minimize skin inflammation and hyperpigmentation.

In a further aspect of the present invention, it is provided a method for identifying compounds expressed by fetal tissues for promoting skin regeneration, compositions comprising one or more of the compounds thus identified, and methods of using the compositions for promoting skin regeneration. The method may further include isolating the compound expressed by fetal tissue, identifying the compound, recombinantly expressing the compound, and then applying the compound to the skin of a mammal.

In still a further embodiment of the present invention, a method of promoting skin regeneration includes comparing compounds expressed by adult tissue and compounds expressed by fetal tissue. Compounds expressed only in adult tissue are selected and other compounds are selected to block expression of the compounds expressed only in adult tissue. The blocking compounds are then applied to skin of a mammal.

Cosmetic skin care compositions are also provided that may include a compound expressed by fetal tissues. Other skin care compositions are provided that may include a proteoglycan such as FM, an enzyme such as chondroitinase B, and an enzyme such as MMP-1.

All percentages and ratios used herein are by weight of the total composition and all measurements made are at 25° Celsius, unless otherwise designated. In certain instance compositions containing enzymes may be expressed by units of specific activity (IU) for a given weight (e.g., IU/mg) or a given volume (e.g., IU/ml)

The compositions of the present invention are useful for topical application and for promoting skin condition. The compounds expressed by fetal tissues can be used as individually purified or partially purified or used directly without purification in the form of cell lysates, extracts, and culture media. In one embodiment of the present invention, compounds expressed by fetal cells or tissues may be isolated directly through tissue culture media or cell lysates and further concentrated or purified. Although individual identification or purification of compounds expressed by fetal tissues may be useful, the application of this invention does not require the individual identification or purification of the compounds. The tissue culture media or cell lysate, which may or may not be further concentrated or purified, may then be formulated into cosmetic compositions to improve the condition of skin.

In a representative embodiment, the composition may comprise: a) from about 0.0001% to about 10% by weight of the proteoglycan compound which is purified, and about 0.1% to about 80% by weight of a cell lysate, extract, or media enriched with the proteoglycan compound; b) from about 0.1% to about 10% by weight of hyaluronic acid; c) from about 0.000001% to about 10% by weight of at least one additional skin care active; and d) a carrier which can be a cosmetically acceptable carrier, a dermatologically acceptable carrier, a pharmaceutically acceptable carrier, a vesicular delivery system, and combinations thereof.

A. Compounds Expressed by Fetal Tissues

Early gestation fetal skin has an innate ability to heal through a process of true tissue regeneration rather than scar formation. Non-coincidentally, the process of tissue regeneration is also characterized by a paucity of inflammation. Thus, the use of a fetal skin model can be used to identify molecules that are important to the inherent ability of early gestation fetal skin to heal through regeneration rather than scar.

It is well documented in the art that fetal skin is fundamentally different from adult skin. For instance, after injury, adult skin repairs through marked inflammation and scar formation, a process characterized by the replacement of injured tissues with a disorganized deposition of collagen and various ECM components, referred to collectively as a "scar." In contrast, fetal skin repair occurs by cellular regeneration and restoration of normal skin architecture through organized deposition of collagen and ECM components to effect scarless repair with minimal inflammation (Mackool, R. J., Gittes, G. K., and Longaker, M. T. Scarless healing. The fetal wound. *Clin Plast Surg* 25:357-365, 1998). Studies have shown that the capabilities for scarless skin repair is one quality of fetal skin, and does not require the fetal immune system, fetal serum, or amniotic fluid (Bleacher J C, Adolph V R, Dillon P W, Krummel T M. Isolated fetal mouse limbs: gestational effects on tissue repair in an unperfused system. *J Pediatr Surg* 28: 1312-4; discussion 1314-5. 1993; Ihara S, Motobayashi Y. Wound closure in fetal rat skin. *Development* 114: 573-82. 1992). For example, isolated human fetal skin transplanted into athymic mice heals without producing typical scar tissue (Adzick N S, Lorenz H P, *Ann Surg* 220: 10-8. 1994).

Accordingly, specific molecules or compositions in regenerating fetal skin that are minimally present or not present at all in non-fetal skin (e.g., adult skin) are important in regenerating and promoting the condition of skin. Specifically, given the lack of significant inflammation in fetal skin, some of these molecules or compositions may also exert anti-inflammatory effects by preventing or minimizing inflammation. Also, given the lack of unorganized fibrous tissue deposition and organization in fetal skin, some of these molecules or compositions may also prevent excessive ECM production and/or promote ECM organization with restoration of normal collagen architecture (Whitby D J and Ferguson M W, *Development* 112:651-668, 1991).

Although a method for identifying genes important for skin ageing and/or skin stress (WO 02/053773 A3) and genes important for skin homeostasis (WO 02/053774 A3) has been disclosed in the prior art, the methods involved are completely different from the present invention. For instance, it has been demonstrated that the capacity for tissue regeneration and scarless repair is confined to specific time points during the fetal period (Ihara S, et al., *Development* 110: 671-680, 1990). Only early gestation mammals have the capacity to heal without scar. Late gestation fetuses and neonatal animals have already lost the capacity for tissue regeneration and exhibit and "adult-type" wound healing response characterized by scar (Soo C, et al., *Am J of Pathol.* 157:423-433. 2000). Thus from a molecular gene screening perspective, the comparison of "old and young skin" as specified in WO 02/053773 A3, would not identify the genes necessary for tissue regeneration as that capacity is already lost in late gestation fetuses and certainly lost in "young" skin. This is supported by the observation that cleft lip repair in infants with "young" skin is followed significant scar formation, and that the only instance of scarless cleft lip repair has been in early gestation fetal animal models (Longaker M T, et al., *Plast Reconstr Surg* 90:750-756, 1992). The prior art does not describe using fetal tissues and wound models for identification of compositions, especially of cosmetic compositions, to improve the condition of skin. In addition, the prior art as stated in WO 02/053773 A3) does not describe a skin regenerative formulation of compositions comprising compounds expressed by fetal tissues.

a) Methods for Preparation of Fetal Tissue in a Fetal Model

Figure 1:
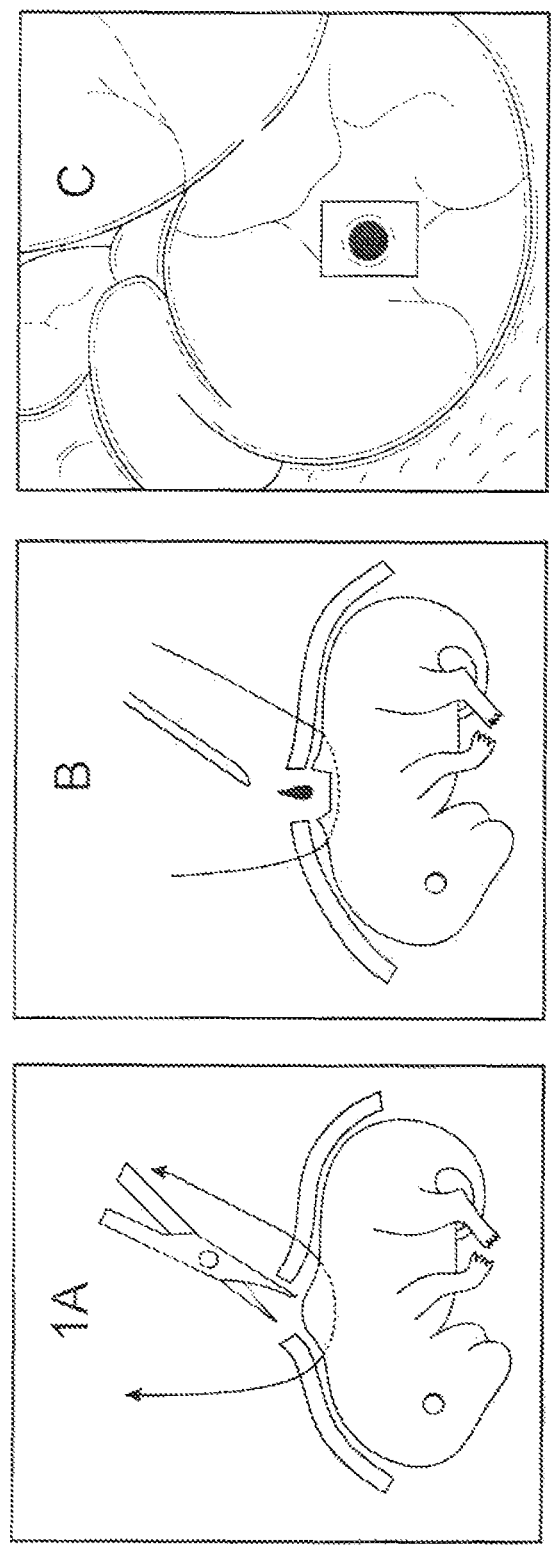
FIG. 1 shows the operative procedure for the fetal wound model. A. A small part of the antimesenteric surface of the uterus is incised and a purse-string suture is placed around the incision. B and C. A full thickness wound is created on each embryo by excising a 2 mm disc of tissue. Blue or green vital stain is applied immediately after wounding for later wound identification.

Female Sprague Dawley (SD) rats (~300 gm) were mated. Detection of a vaginal plug as evidence of pregnancy was considered day 0.5 of gestation (term=21.5 days). For creation of the fetal wounds, pregnant rats were anesthetized on days 16 and 18.5 or 19 of gestation. Fetal rat skin transitions from scarless fetal-type repair to adult-type repair with scar between day 16 (E16) and day 18 (E18) of gestation (term=21.5 days). E19 fetal rats were chosen to avoid potential overlaps with the E16 to E18 transition period. Anesthesia consisted of 1% Ketamine at a dose of 10-20 mg/kg and 0.1% Xylazine at a dose of 0.3 mg/kg. The pregnant animals were shaved and a midline laparotomy performed. Each uterine segment was externalized and a 7-0 nylon purse-string suture was placed through all layers of the uterine wall on the non-placental surface. The myometrium and amniotic sac was then incised within the purse-string utilizing microsurgical scissors. Subsequently, a 2-mm excisional wound was made on the dorsum of the fetuses by grasping the skin with microsurgical forceps and excising the skin with scissors. Blue or green vital stain was applied to the excisional sites for later wound identification. Warm sterile normal saline was then applied through the hysterotomy and the purse-string closed (FIG. 1). The maternal fascia and skin was then closed in two layers using 2-0 synthetic absorbable suture.

For histology, E16 and E19 fetal wounds were harvested at 12, 24, 36, 48, and 72 hours post-operatively. Non-wounded skin from each of the wound harvest time points were used as controls (e.g., E17 control skin for E16+24 hours wounds). A total of four animals from two separate pregnancies were utilized for each time point. All tissue specimens were fixed in 4% paraformaldehyde, dehydrated through graded ethanol, embedded in paraffin, and cut into 5 μm sections for Hematoxylin and Eosin (H & E) staining and immunohistochemistry, or into 7 μm sections for confocal laser scanning (CLSM) microscopy.

For RNA analysis, E16 and E19 fetal wounds were harvested at 24 and 72 hours after injury. Non-wounded skin from each of the wound harvest time points were used as controls (e.g., E19 control skin for E16+72 hour wounds). A total of 20 wounds were utilized for each time point. The isolated tissue was immediately frozen in liquid nitrogen and stored at −70° C. until RNA extraction.

b) Methods for Confirmation of Tissue Regeneration in a Fetal Model

Figure 2:
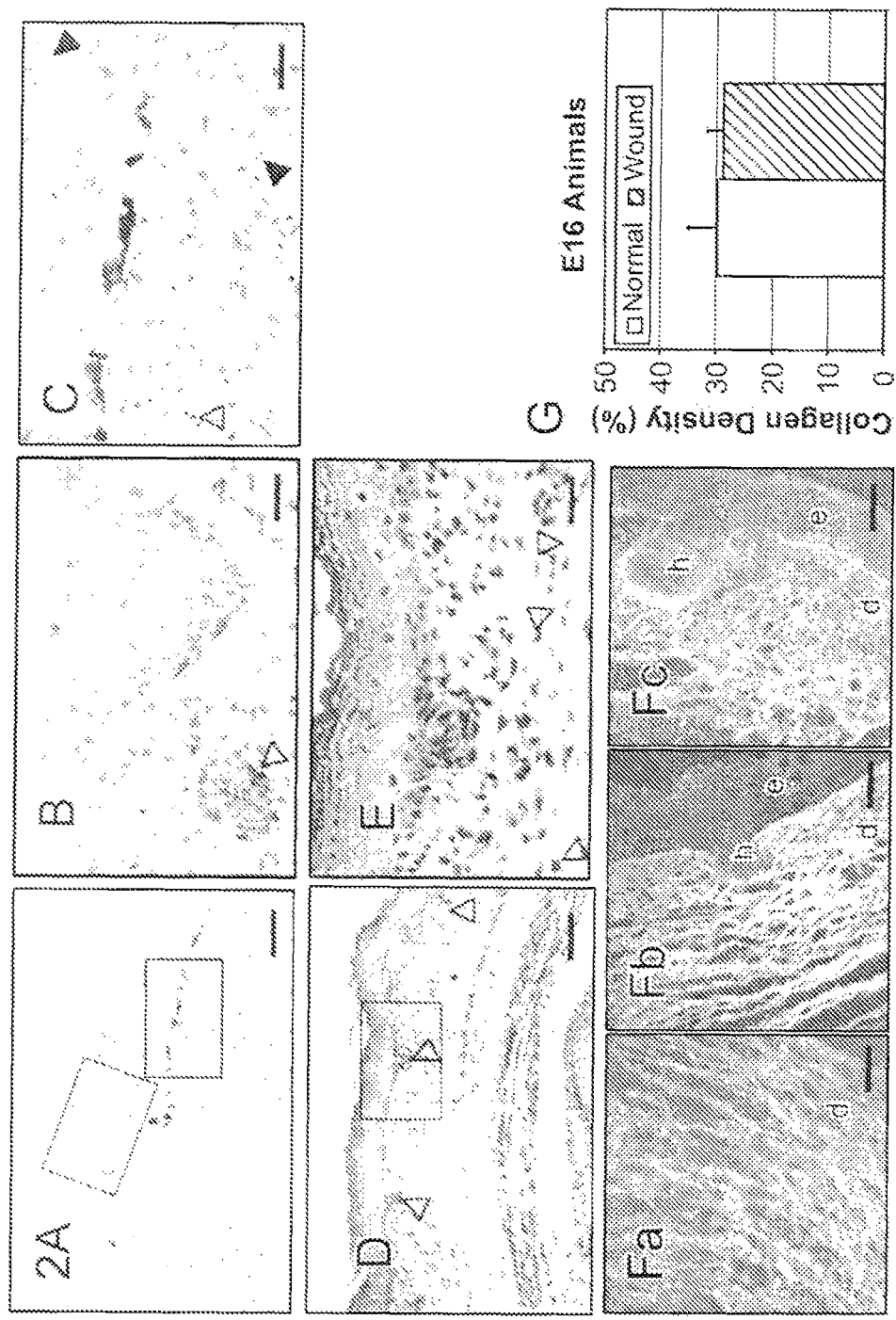
FIG. 2 shows the H&E staining of wounded E16 rat skin with regenerative repair. A. 24 hours post-injury, 100×. There is minimal inflammatory infiltrate. B. 24 hours post-injury, 400×. The presence of blue vital dye in hair follicles near the migrating epithelial edge suggests concurrent hair follicle regeneration with wound re-epithelialization (black open arrow). C. 24 hours post-injury, 400×. Neutrophils (black solid arrows) and lymphocytes (black open arrow) are the predominant cells of the wound periphery and the center of the wound, respectively. D. 72 hours post-injury, 100×. The wound is entirely healed with complete regeneration of the normal skin architecture. Normal distribution of hair follicles (black open arrows) are observed in the dermis. E. 72 hours post-injury, 400×. At higher magnification, the previous wound site, as indicated by the presence of blue vital stain in the dermis (black open arrows), is indistinguishable from the non-wounded skin. F. Confocal microscopic view of wounded E16 rat skin (Fa through Fc). Fa. 48 hours post-injury, 630×. Note the organized appearance of the collagen fibers with a reticular lattice structure. Fb. 72 hours post-injury, 630×. The wound site is completely re-epithelialized with complete restoration of normal skin collagen architecture and hair follicle regeneration. Fc. Non-wounded E19 skin [i.e., E16+72 hours], 630×. No difference is observed between E16 skin, 72 hours post-wounding, and non-wounded E19 skin. e: epidermis. h: hair follicle. d: dermis. Scale bars: A,D, 200 µm; B,C,E, 50 µm; Fa-Fc, 32 µm. G. There is no significant difference in total collagen density between E16 fetuses 72 hours post-injury and non-wounded E19 (E16+72 hours) fetuses (p>0.05).
Figure 3:
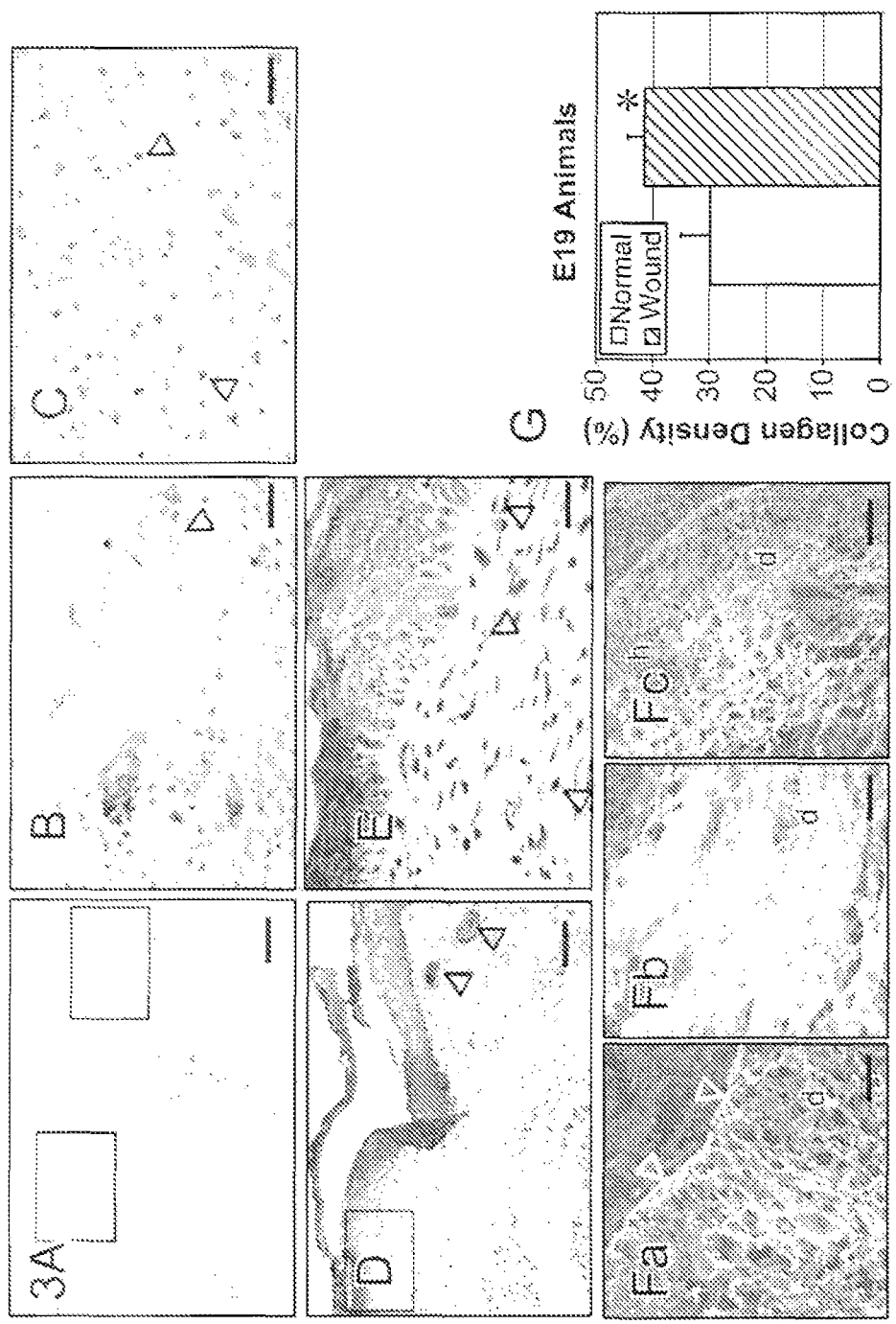
FIG. 3 shows the H&E staining of wounded E19 rat skin with non-regenerative repair. A. 24 hours post-injury, 100×.

Both H & E staining to evaluate overall wound appearance and CLSM to analyze collagen architecture and fibril arrangement were used (FIGS. 2 and 3). CLSM techniques were performed as previously described (Beanes S R, et al., *Plast Reconstr Surg.* 109:160-170., 2002).

Total collagen density per healed wound site was calculated using Image Pro® Plus by dividing total collagen surface area by total wound surface area (Media Cybernetics, Silver Spring, Md.) for both E16 (n=10) and E19 (n=8) wounds at 72 hours after injury. For comparison, total collagen density in non-injured skin from age-mated controls [e.g., E19 (E16+72 hours) and neonatal day 1 (E19+72 hours) animals] was also determined. Means and standard deviations were calculated and unpaired two-tailed Student's t test was performed to detect statistically significant differences in total collagen density. A p value of <0.05 was considered significant.

As can be seen from FIG. 2A-E, E16 wounds demonstrated regenerative scarless repair on H&E with minimal dermal inflammation and dermal cellularity and organized collagen architecture on CLSM that was comparable to normal, unwounded skin (FIG. 2F). Digital imaging analysis verified that 72 hour post-injury E16 wounds and non-injured E19 (E16+72 hours) skin did not display significantly different collagen densities (p>0.05) (FIG. 2G). In contrast, E19 wounds demonstrated non-regenerative repair with scar and absent hair follicle regeneration as well as increased and prolonged inflammation and increased dermal cellularity (FIG. 3A-E). CLSM revealed a disorganized collection of dense, heterogeneous collagen fibrils in the completely healed wound (FIG. 3F). Digital imaging analysis verified that there was significantly increased collagen density in E19 wounds 72 hours after injury relative to non-wounded neonatal day 1 skin (E19+72 hours) (p=0.00043) (FIG. 3G). These studies indicate that early gestation E16 wounds exhibit a capacity for scarless regenerative repair that is lost in late gestation E19 wounds. Human fetal skin from 15 to 22 weeks ($2^{nd}$ trimester) also exhibited a capacity for scarless regenerative repair. (Reviewed in Dang C, et al., *Clin Plast Surg.* 30:13-23, 2003).

c) Method for Direct Compound Derivation from Human Fetal Tissue Culture Systems As discussed above, human fetal skin between 15 to 22 weeks possesses the capability for scarless skin repair and tissue regeneration. Thus, non-genetically modified compounds expressed by fetal tissues may be obtained from fetal skin organ cultures, two- or three-dimensional fetal cell cultures, and media from cultured fetal cells/tissues. These compounds may be in the form of lysates, extracts, or media. Methods of cell and tissue culturing, as well as methods of obtaining cellular lysates or extracts, are well known in the art. (Refer to Pollard J W, Walker J M (1997) Basic cell culture protocols, 2nd ed. Humana Press, Totowa, N.J. for more specific details on cell culture). Human fetal cell culture media may be isolated and the resultant supernatant processed. Cell culture supernatant processing is well known to those of ordinary skill in the art and can include, but is not limited to, concentration of the supernatant, specific compound purification from the supernatant, and sterilization of the supernatant. The method of cell culture supernatant processing should ensure optimal preservation of biologic activity of the compounds expressed by fetal tissues. Aseptic processing and other efforts to promote sterilization are also desirable and needed. The following are examples intended to clarify, but not limit, the scope of the invention.

Human Fetal Cell Culture

Fetal skin fibroblasts may be isolated from fetal skin specimens by placing small strips of fetal skin (dermal side down) into a cell culture plate. Fetal skin fibroblasts migrate from the pieces of skin and attach to the culture plate. Following attachment of the fibroblasts to the culture plate, the pieces of skin are then discarded. The fetal skin fibroblasts are allowed to grow to the desired confluency and are isolated according to standard techniques.

Human Fetal Cell Media Preparation

Fetal cell media (or supernatant) can be obtained by pouring or aspirating the fluid from the fetal tissue or cell cultures. Following removal, the resulting supernatant can be further processed. Examples of such processing may include, but are not limited to, concentration by a water flux filtration device or defiltration (see section below "Example of Protein Purification from Fetal Cellular Media or Lysate" for more information about further processing).

Human Fetal Cell Lysate Preparation

After allowing fetal skin fibroblasts to grow to 70-80% confluency in a cell culture plate, cell lysate preparation is carried out as follows: (1) culture plates containing the fetal fibroblasts are thoroughly washed in phosphate buffered solution ("PBS") in order to remove serum; (2) the fetal fibroblast cells are then incubated approximately 3 minutes with a dissociating enzyme such as trypsin to facilitate detachment from the culture plates; (3) the detached cells are then pelleted by centrifugation and then lysed using a detergent such as sodium dodecyl sulfate ("SDS"). The supernatant is then dialyzed to remove the traces of SDS.

Intracellular products are also isolated by chemical (e.g., organic solvents), enzymatical (e.g., lysozyme and EDTA), mechanical, or physical cell disruption methods (e.g., homogenization, ultrasonication, high pressure homogenization, agitation with abrasion). Combinations of mechanical and non-mechanical methods are also contemplated.

Protein Purification from Human Fetal Cellular Media or Lysate

Purification of the extracellular (cellular media) or intracellular (lysate) products can be performed using a variety of methods to facilitate product isolation or to remove undesired contaminants. One method is solid-liquid phase separation (e.g., centrifugation/sedimentation, extraction, filtration). Another method is concentration (e.g., evaporation, ultrafiltration, adsorption, precipitation). Yet another method is chromatography (e.g., size exclusion, ion-exchange chromatography, chromatofocusing, hydrophobic interaction, affinity chromatography, immobilized metal-ion affinity chromatography, covalent chromatography.) These techniques are all readily carried out by one of ordinary skill in the art. Sterilization techniques such as filtration or heat or irradiation can also be applied if necessary. (Refer to Ratledge C, Kristiansen B (2001) Basic biotechnology, 2nd ed. Cambridge University Press, Cambridge, U.K. for more information on protein purification).

d) Method for Indirect Compound Derivation from Fetal Wound Models through Gene Recombinant Technology In another embodiment of the present invention, compounds expressed by fetal tissues or conditions that promote expression of these compounds are identified in mammalian skin (human or non-human). Fetal tissues and cells display distinctly different patterns of gene expression from adult cells. At the protein level, this can result in differential production of distinct ECM components, growth factors, cytokines, and enzymes (Sullivan K M, Lorenz H P, Meuli M, Lin R Y, Adzick N S. A model of scarless human fetal wound repair is deficient in transforming growth factor beta. *J Pediatr Surg* 30:198-202; discussion 202-3, 1995). For instance, fetal skin fibroblasts produce higher ratios of type III relative to type I collagen and different profiles of proteoglycans, as well as more hyaluronic acid (Mast B A, Diegelmann R F, Krummel T M, Cohen I K. Scarless wound healing in the mammalian fetus. *Surg Gynecol Obstet* 174:

441-51. 1992). Proteoglycans are core proteins carrying one or more GAG chains with key roles in ECM assembly, cellular interactions, and growth factor storage (Ruoslahti E. Proteoglycans in cell regulation. *J Biol Chem* 264:13369-72, 1989).

Gene expression differences between fetal and adult tissues may be identified through standard molecular biology techniques. For example, Northern blot, subtractive hybridization, differential display PCR, microarray, and real time PCR may be utilized to identify gene expression differences. (The following are sample references for some of the various techniques: DD-PCR—Liang L, Arthur B P. Differential display of eukaryotic messenger RNA by means of the polymerase chain reaction. *Science* 257:967-971, 1992; Microarrray—Zhang X, et al., Craniosynostosis in transgenic mice overexpressing Nell-1. *J Clin Invest* 110: 861-70. 2002; Subtractive hybridization—Diatchenko L, et al., Suppression subtractive hybridization: a method for generating differentially regulated or tissue-specific cDNA probes and libraries. *Proc Natl Acad Sci USA* 93: 6025-30. 1996). Using the various differential gene expression identification techniques, a molecular "blue print" of the specific events in fetal skin regeneration can be elucidated and specific molecules identified as being up-regulated or down-regulated during fetal regenerative repair. Please refer to FIGS. 4-7 for examples of specific primer PCR based techniques of candidate gene screening.

Once identified, up-regulated molecules in early fetal, but not late fetal or adult tissues or cells may then be isolated and identified for subsequent product development. These up-regulated molecules may be "added back" to confer more "fetal-like" properties to adult skin. Conversely, molecules up-regulated in late fetal or adult tissues, but not early fetal tissues, may also be identified for subsequent product development. One may "block or inhibit" the identified up-regulated molecules in adult tissues to confer more "fetal-like" properties to adult skin.

The following are intended to clarify, but not limit the scope of the present invention. The molecules to be "added back" may be directly derived from fetal tissue or fetal cell culture media, lysates, or extracts (see the above discussion, supra). Alternatively, the molecules to "add back" may be "recombinantly expressed" (with or without preceding genetic modification) in genetically engineered cells for the purpose of increasing its expression. Up-regulated molecules in fetal cells or tissues may then be utilized in skin compositions individually or in combination. Conversely, up-regulated molecules identified in adult, but not fetal tissues (i.e., the molecules to "block or inhibit") may be targeted using antisense RNA molecules or known inhibitors or modulators (e.g., chondroitinase B for modulation of dermatan sulfate). The antisense RNA molecules or known inhibitors may then be subsequently used in the skin care composition.

Screening Normal Rat Fetal Tissue as a Function of Gestation

Gene expression screening of uninjured fetal skin as a function gestation may allow for the identification of molecule important for fetal skin homeostasis in the absence of injury. FIG. 4 shows the downregulation of FM and upregulation of decorin with increasing gestational age and loss of regenerative healing, which are unexpected to one with ordinary skill in the art, showing decorin upregulation temporally associates with non-regenerative repair in late gestation fetuses. The other molecules screened by this methodology [i.e., TGF-beta ligands and receptors as well as latent TGF-beta binding protein-1 (LTBP-1)] are included as examples of screening using specific primer based PCR.

Screening Wounded Rat Fetal Tissue

Figure 7B:
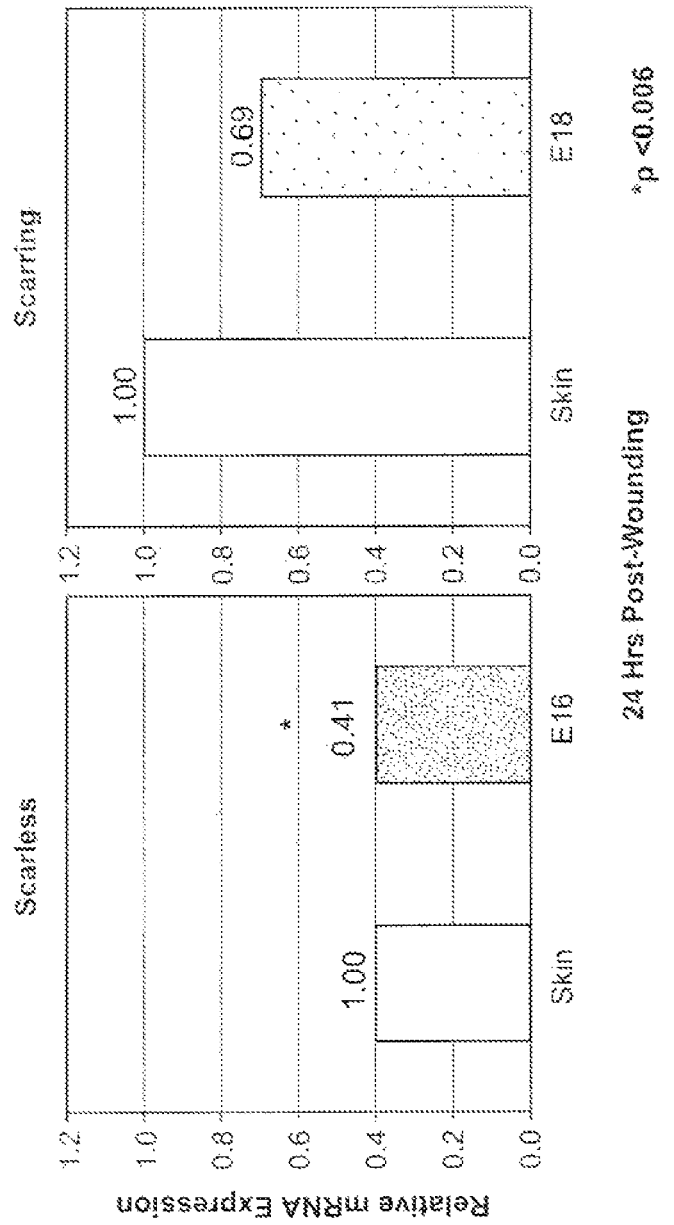

Gene expression screening of injured E16 relative to E19 fetal skin allows for potential identification of molecules that are critical to skin regeneration. FIG. 5 shows the results of PCR based screening for MMPs and TIMPs. Scarless wounds are characterized by relatively higher MMP-1 and MMP-9 expression and less TIMP-1. This demonstrates that relatively increased ECM degradation relative to excessive ECM deposition is important to scarless repair. Since excessive accumulation of ECM constitutes on essential component of a scar, compounds that can prevent excessive ECM deposition and promote ECM degradation such as MMPs may be useful to skin regeneration after injury characterized by scar formation. FIG. 6 shows the results of PCR based screening for FGFs. Scarless wounds are characterized by minimal FGF induction in the initial 48 hours after injury relative to wounds that scar. In particular, FGF-2 (which is bFGF) is relatively decreased in scarless fetal wounds. This suggests that modulation of bFGF may be useful to skin regeneration. FIG. 7 shows the results of PCR based screening for decorin and FM. It shows that FM, but not decorin, is up-regulated in E16 regenerative wounds, indicating that modulation of FM, rather than decorin, can be used to promote skin regeneration.

Individual Gene Cloning

Gene cloning techniques are well described in the art (Please refer to Wu W. *Methods in Gene Biotechnology*. Boca Raton: CRC Press, 1997 for more information). Briefly, for genes in which the coding sequence is known, specific primer PCR based techniques may be used for gene cloning. From these sequences, PCR primers can be designed that flank the coding sequence. After amplification, PCR products can then be ligated into various expression plasmids for bacterial, yeast, or mammalian cells. For genes in which the coding sequence is unknown, which is often the case for genes sequences identified using differential display, isolation of the full length cDNA clones can be accomplished by 5' Rapid Amplification of cDNA Ends (RACE) as previously described (Soo C, et al., *J Cell Biochem*. 74:1-10, 1999). For instance the complete cDNA sequence for human FM was obtained through GenBank by the following accession numbers: NM_002023, BC035281, or X75546. The full-length coding cDNA for the human FM was amplified by reverse transcription-polymerase chain reaction (RT-PCR) from the total RNA of human fibroblast. The specific primers used for the PCR were designed on the basis of published human FM cDNA sequence on GenBank Accession No NM_002023 and the 1.1 kb PCR fragment was confirmed by full-length sequencing.

Mammalian Expression Plasmid Construction and Expression for FM

The p3xFLAG-CMV-14 (Sigma) expression vector for the mammalian system was chosen by virtue of its convenience of subsequent protein purification. The 3xFLAG sequence was attached at the C-terminal end of the human FM cDNA insect in frame to render the production of C-terminal flag-tagged recombinant protein. The final construct of HFM expression plasmid, p3FLAG-CMV-HFM, was further confirmed by selective restriction digestion and DNA sequencing.

The CHO-K1 cell line (ATCC, Manassas, Va.) was used for the production of recombinant human FM (rhFM). The stable transfected cell line was established following extensive selection with G418 in the medium and screening by the immunofluorescent cytochemisty with anti-Flag antibody for the expression of the recombinant protein. The rhFM was purified through affinity chromatography of anti-flag agarose column with competitive elution by 3XFLAG peptide to maintain the rhFM in natural form. The purified protein contains native KS side chains which was confirmed by Western blot in terms of the molecular size. The ability of rhFM to bind TGF-β1 and bFGF was verified by ELISA binding assay. The hydrophilic flag peptide of the rhFM can be readily removed by digestion with enterokinase if necessary.

Bacterial Expression Plasmid Construction and Expression for FM

The pFLAG-MAC (Sigma) expression vector for the *E. coli* system was used for its easy purification of the recombinant protein from the bacterial cytoplasm. Within this amino-terminal flag-tagged vector, the human FM cDNA insert was driven by the tac promoter and the flag tag in the fusion protein can be removed with the enterokinase if necessary. As same as in the mammalian system, the full-length coding cDNA fragment of the human FM for the construct was amplified by RT-PCR from the total RNA of human fibroblast. The final construct of HFM expression plasmid, pFLAG-MAC-HFM, was further confirmed by selective restriction digestion and DNA sequencing.

The *E. coli* strain BL21 was used for the production of rhFM. The transformation and selection of the positive colony was carried out under the standard protocols. The large scale bacterial culture with an OD600 of about 2.0 was harvested by centrifuge at 5,000×g for 10 minutes. The bacterial cells were lysed with CelLytic B lysis buffer (Sigma) supplemented with DNase I at 5 ug/ml. The rhFM was purified from the crude extract of bacteria through affinity chromatography of anti-flag agarose column with competitive elution by 3XFLAG peptide. The molecular weight and purity of the rhFM was confirmed by Western blot. The ability of rhFM to bind TGF-β1 and bFGF was verified by ELISA binding assay. The hydrophilic flag peptide of the rhFM can be readily removed by digestion with enterokinase if necessary.

Recombinant Expression of Individual Genes in Prokaryotic Cells

A vector containing the gene of interest is constructed for later insertion into prokaryotic cells. A strong promoter (such as T7) or a Lac promoter can be used to induce high transcription efficiency. A potential affinity binding sequence such as a histidine affinity tag will be inserted into the N-terminal having a protease cleavage site. Additional sequences such as maltose binding protein, may be inserted to increase solubility. (Hildebrand A, Romaris M, Rasmussen L M, Heinegard D, Twardzik D R, Border W A, Ruoslahti E. Interaction of the small interstitial proteoglycans biglycan, decorin and FM with transforming growth factor beta. Biochem J 302 (Pt 2): 527-34, 1994).

Recombinant Expression of Individual Genes in Eukaryotic Cells

Eukaryotic systems such as yeast, baculovirus, and mammalian systems allow post-translational modification of gene products. A strong promoter such as AOX1 in yeast, or cytomegalovirus ("CMV") in mammalian cells can be used to induce high transcription efficiency. An affinity tag can be inserted at either the N or C terminal of the translational product. Secretory sequences can also be inserted at the N-terminal to increase the secretion of desired recombinant molecules into the cell culture medium.

Large scale expression of recombinant proteins can also be performed through established commercial companies using bioengineered plant systems (e.g., www.VentriaBio.com).

Binding Assay of Flag-Tagged Human FM (HFM) and Decorin (HDC)

Flat bottom multi-well plates were coated with human recombinant TGF-beta1 (Sigma) or human recombinant bFGF (Sigma) at 50 μl/well (0.5 μg/ml) diluted in coating buffer (0.5 mM sodium carbonate buffer, pH9.3) overnight at 4 C. The coated wells were then emptied and 200 μl of binding buffer (50 mM Tris/HCl, pH7.4, 150 mM NaCl, 2% BSA and 0.05% Tween20) was added to each coated well to block non-specific binding sites by incubation for 2 hours at 37 C. The wells were emptied and washed three times by entirely filling each well with wash buffer (PBS, 0.1% Tween20) and then flicking out the contents and slapping the plate upside down three times on a paper towel. The affinity purified flag-tagged human FM and decorin from plasmid transfected CHO-K1 cells were added in a 100 μl/well of binding buffer and incubated for 1 hour at 37 C followed by overnight at 4 C. The wells were emptied and washed as before and incubated with 100 μl/well of anti-flag biotinylated M2 mAb (Sigma) diluted at 1 μg/ml in TBS-Ca buffer (50 mM Tris/HCl, pH7.4, 150 mM NaCl, and 1 mM CaCl2) for 1.5 hours at room temperature. The wells were emptied and washed again as before and 100 μl/well of detecting Streptavidin-HRP (Dako Corp.) was incubated for another 1.5 hours at room temperature. The wells were washed four times and emptied completely before adding 100 μl/well of developing buffer (100 μg/ml Tetramethylbenzidine, 0.003% H2O2 in sodium acetate buffer, pH6.0). The reaction was stopped by adding 100 μl of 1N hydrochloric acid to each well after 15-30 minutes for development. Binding capacity of purified human FM and decorin to the surface-immobilized hrTGF-beta1 or hrbFGF was determined by the absorbance value at 450 nm using an ELISA plate reader (Fisher). All the experiments were performed in triplicate. Both flag-tagged bacterial alkaline phosphatase (BAP-Flag)(Sigma) and purified lysate from parental CHO-K1 cells (ConL) were used as negative controls.

Readings at 450 nm for TGF-beta1 binding (triplicate)
Blank 0.121, 0.111, 0.113
ConL 0.151, 0.163, 0.164
BAP 0.120, 0.137, 0.130
HDC 0.205, 0.207, 0.206
HFM 0.787, 0.722, 0.741
Readings at 450 nm for bFGF binding (triplicate)
Blank 0.123, 0.107, 0.123
ConL 0.207, 0.242, 0.198
BAP 0.138, 0.120, 0.122
HDC 0.233, 0.282, 0.244
HFM 0.796, 0.729, 0.763

The binding of HSM to TGF-beta1 was well described in the art. It is not known in the art that HFM is equally capable of binding to bFGF. This ability of HSM to bind bFGF is particularly remarkable as the interaction of bFGF with keratan sulfate SLRPs such as FM has not been described. To date, the only known interaction between SLRPs and bFGF has been with dermatan sulfate moieties present on decorin and not the decorin core protein itself (Zamfir A, et al., *Glycobiology*. 13:733-742, 2003). Since bFGF is also a potent mitogen for fibroblasts, this ability of FM to bind bFGF can be particularly useful in methods to treat conditions of excessive fibroblast proliferation as in scars or to treat conditions of excessive melanocyte proliferation or activity as in hyperpigmentation. Furthermore, since UVR results in bFGF induction and bFGF, among other effects, is known to stimulate plasminogen activator and collagenase activity that facilitate ECM breakdown (Reviewed in Abraham J A and Klagsbrun M. Modulation of wound repair of members of the fibroblast growth factor family. Ed. Clark RAF. *The Molecular And Cellular Biology Of Wound Repair*. Vol. xxiii. New York: Plenum Press, pp. 195-248, 1996), modulation of bFGF activity by FM may also prevent or minimize the effects of photoaging including collagen disorganization.

Genetic Modification Prior to Recombinant Expression

Mutations or genetic modifications can be created in both the non-coding or non-essential regions of a defined gene sequence (e.g., promoter region, untranslated 3' regions) as well as the coding or essential regions of a defined gene sequence. By "essential" it is meant the portion(s) of the gene that is/are critical to the gene carrying out its intended function. Genetic modifications in the non-coding regions are generally made to enhance the overall transcriptional or translational efficiency of a gene and to increase the ease of purification of the final protein product—these changes generally do not affect the functional characteristics of the gene. In contrast, genetic modifications of the coding region are generally made for purposes of modifying the translated product to increase or decrease desired functions of the gene (e.g., modify affinity for target molecule, modify skin penetration characteristics, modify post-translational processing, modify half-life of molecule). Both techniques for non-coding or coding modification are all well described in the art.

B. Small Leucine Rich Proteoglycans

SLRPs are a class of compounds with different functions that can be used to promote skin regeneration. Although FM was mentioned for reduction of dermal scarring and wound contraction, by definition these are conditions that occur with dermal injury. There are many instances were application of FM or equivalent may be desirable to improve the condition of skin that do not involve the requirement for reduction of dermal scarring or wound contraction.

a) Treatment of Intact, Aged Skin to Promote Skin Regeneration

It is known in the prior art that decorin may improve the appearance of aged skin. But as stated above, decorin and FM are different classes of SLRPs with different functions. In addition FM null mice did not have obvious skin deficits and there is minimal FM expression in non fetal skin. Therefore it is completely unexpected and novel that FM would have such a central role in collagen organization and skin regeneration.

Although boosting decorin synthesis in skin by topical application of conjugated linoleic acid, petroselinic acid, and other compounds (U.S. Pat. Nos. 6,551,602; 6,455,057; 6,440,434; 6,423,325; 6,287,553; 6,042,841) or actual use of decorin in cosmetic or dermatologic compositions (20030124152) has been described in the prior art, there is no mention of the use of FM. The existing prior art has focused on decorin because decorin production by fibroblasts appears to diminish with age and photo damage, and because lack of decorin in skin is associated with decreased tensile strength and skin fragility (Takeda K, et al., *J Cell Physiol.* 153:450-459, 1992; Carrino D A, et al., *Arch Biochem Biophys.* 373:91-101, 2000). Thus, several patents exist that specifically mention decorin, but not other SLRPs such as FM, in the context of preventing or treating skin aging.

The use of FM to improve the condition of skin is not obvious from the existing prior art. For instance, as expected from the close relationship between decorin and skin, decorin knockout mice demonstrate distinct skin fragility. Meanwhile, FM knockout mice as expected did not demonstrate any discernable skin abnormalities and minimal FM has been detected in skin adult skin. Moreover, in injured adult skin decorin, but not FM, is up-regulated—indicating a close relationship between decorin expression and the adult non-regenerative repair response. In addition, FM and decorin belong to two different classes of SLRPs that bind to different regions of the collagen molecule.

Therefore, the upregulation of FM, but not decorin, during regenerative repair in early gestation fetal skin as evidenced by organized collagen deposition, while non-regenerative repair with disorganized collagen arrangement was not accompanied by FM upregulation in late gestation fetal skin (see FIGS. 4 and 7). Moreover it was even more surprising that elimination of FM alone by using anti-FM antibodies was enough to prevent organized collagen deposition in early gestation fetal animals that normally exhibit scarless repair and that addition of FM alone was enough to promote organized collagen deposition in late gestation fetal animals that normally exhibit repair with scar (FIGS. 8 and 9). Consistent with the previous data on the lack of excessive matrix accumulation in scarless fetal wounds, type I collagen mRNA expression was decreased in late gestation wounds following FM treatment (FIG. 10). Application of FM to adult wounds also significantly improved overall dermal structure and collagen organization (FIG. 11). This confirms that our method to use compounds from fetal tissues, or identified through fetal tissues, to improve skin condition is applicable to adult skin.

b) Treatment of Non-Intact Skin with Epidermal Injury

The use of decorin, or functionally equivalent molecules such as FM, to prevent dermal scarring or wound contraction as been well described in the prior art. A scar is a fibrous or connective tissue deposition that by definition only occurs with dermal injury. Dermal injury initiates a cascade of wound healing responses that involves hemostasis, inflammation, proliferation, and remodeling. Normal dermal injury repair is characterized by connective tissue deposition by fibroblasts and wound contraction by myofibroblasts that ultimately result in scar (Mast B A. The skin. In Wound Healing: Biochemical and Clinical Aspects. Eds. Cohen K I, Diegelmann R F, Lindblad W J. Philadelphia: WB Saunders Company, p. 344-355, 1992). For instance, U.S. Pat. No. 6,509,314 teaches that "dermal scarring is a process following a variety of dermal injuries that results in the excessive accumulation of fibrous tissue comprising collagen, fibronectin, and proteoglycans. The induction of fibrous matrix accumulation is a result of growth factor release at the wound site by platelets and inflammatory cells. The principle growth factor believed to induce the deposition of fibrous scar tissue is . . . TGF-beta. Decorin binds and neutralizes a variety of biological functions of TGF-beta, including the induction of ECM."

In contrast, epidermal injuries alone do not scar or cause wound contraction. Partial thickness wounds such as abrasions or superficial burns do not penetrate the dermis and therefore, neither fibrous or excessive connective tissue deposition (i.e. scar) nor wound contraction plays a role in epithelial healing (Mast B A. The skin. In Wound Healing: Biochemical and Clinical Aspects. Eds. Cohen K I, Diegelmann R F, Lindblad W J. Philadelphia: WB Saunders Company, p. 344-355, 1992). Thus, the normal wound cascade of hemostasis, inflammation, proliferation, and remodeling does apply because first of all, there are no blood vessels in the epidermis to injure. However epidermal injury or irritation can initiate an inflammatory response that can affect melanocytes and Langerhans cells that are contained within the epithelial layer. Stimulation and/or injury to melanocytes can stimulate or disrupt the process of pigment production by melanocytes. Overstimulation of melanocyte pigment production can lead to epidermal or dermal hyperpigmentation, while injury to melanocytes can lead to hypopigmentation. The processes of hyperpigmentation and hypopigmentation directly relate to the process of pigment production by melanocytes and are completely different from the processes of scar formation and wound contraction which are mediated by fibroblasts producing collagen and other ECM components and myofibroblasts, respectively. Thus, because of the completely different mechanisms involved in scar formation or wound contraction relative to pigmentary problems, it follows that use of FM for treatment of potential complications associated with epidermal inflammation or injury is not obvious from the prior art.

c) Treatment to Promote Collagen Organization

With specific regard to intact skin, promotion of collagen organization may potentially be used to treat conditions of disorganized collagen formation such as chronological aging or photoaging. With specific regard to non-intact skin, promotion of collagen organization may potentially be used to treat conditions of disorganized collagen formation such as dermal scarring.

As mentioned previously, the use of decorin, or functionally equivalent molecules such as FM, to prevent dermal scarring (U.S. Pat. Nos. 5,654,270; 6,509,314) or wound contraction as been well described in the prior art (U.S. Pat. Nos. 5,510,328; 5,851,994).

Thus, the prior art teaches that excessive fibrous matrix accumulation is a central component of scar and that this is mediated primarily by TGF-beta. Furthermore, the prior art teaches that improvement of scar by decorin or related molecules is primarily related to the ability to regulate TGF-beta activity. Thus the prior art teaches that decorin or related molecules can modulate the quantity of ECM accumulation. This reduction in the quantity of ECM accumulation will aid the treatment of pathological entities characterized by excessive fibrous tissue deposition such as glomerulonephritis and dermal scar. However, reduction in ECM quantity alone or even inhibition of TGF-beta activity alone is not enough to completely eliminate scar. This is because although TGF-beta is known to have a direct effect on the production of ECM, it has no known effects on the organization of the ECM.

TGF-betas are multifunctional cytokines with widespread effects on cell growth and differentiation, embryogenesis, immune regulation, inflammation, and wound healing (Border W A, et al., *Kidney International Supplement.* 49:S59-61, 1995). In terms of cutaneous repair, TGF-beta1 and TGF-beta2 are known to promote scar, while TGF-beta3 may reduce scar (Lin R Y, et al., *Ann Surg.* 222:146-154, 1995; Shah M, et al., *J Cell Sci.* 108 (Pt 3):985-1002, 1995). TGF-beta has been implicated in the ontogenetic transition from scarless fetal-type repair with minimal inflammation to adult-type, non-regenerative repair with significantly increased inflammation. Adult-type repair with scar is characterized by excessive quantity of matrix deposition and decreased quality of matrix deposition. A number of strategies designed to neutralize TGF-beta1, including antibodies against TGF-beta1 and TGF-beta2, antisense TGF-beta1 oligodeoxynucleotides, and viral gene therapy, have been shown to reduce, but not completely eliminate, scarring in adult animals (Choi B M, et al., *Immunol Cell Biol.* 74:144-150, 1996; Shah M, et al., *Lancet.* 339:213-214, 1992; Shah M, et al., *J Cell Sci.* 107 (Pt 5): 1137-1157, 1994; Isaka Y, et al., *Nat. Med.* 2:418-423., 1996; Elepfandt P, et al., *Neurosci Lett.* 322:107-110, 2002). This indicates that inhibition of TGF-beta activity with its associated reduction in ECM quantity alone is not enough to completely eliminate scar.

It has been shown that deficient TGF-beta1 expression as a sole mechanism for scarless fetal repair is overly simplistic. It has also been shown that even scarless E16 wounds exhibit initial TGF-beta1 and -β2 upregulation after injury (Soo C, et al., *Am J Pathol.* in press). Moreover, although TGF-beta is widely recognized as a pro-fibrotic peptide that can increase the quantity of ECM, there are no data indicating that TGF-beta can directly impact the quality or organization of the ECM. This indicates that other factors directly involved in ECM structure and organization may also be important to regenerative fetal repair.

However, there are other conditions, not necessarily associated with skin injury, that result also in fibrous connective tissue deposition. One example is systemic sclerosis, a connective tissue disease characterized by fibrosis of the skin, subcutaneous tissue, and various internal organs due primarily to excessive accumulation of type I and III collagen (Kuroda K, and Shinkai H., *Arch Dermatol Res.* 289: 481-485, 1997.

Thus, innate or acquired abnormal collagen structure or organization can lead to the dysfunction of various tissues. For instance, mutations in the collagen molecule itself leading to abnormal collagen structure can give rise to various congenital diseases syndromes such as chondrodysplasias, osteogenesis imperfecta, Ehler's Danlos Syndrome, or epidermolysis bullosa (Reviewed in Gelse K, et al., *Adv Drug Deliv Rev.* 55:1531-1546, 2003), while mutations the SLRPs that regulate collagen fibrillogenesis can give rise to various abnormalities such as osteoarthritis, an Ehler's Danlos-like phenotype, muscular dystrophy, and corneal diseases. (Ameye L, and Young M F., *Glycobiology.* 12:107 R-116R, 2002). Meanwhile, injury or disease can lead to acquired disorganization of collagen architecture that then generates further diseases. In these instances, the disorganized collagen can be collectively termed a "scar". Scar formation is central to the pathogenesis of many human diseases, including liver cirrhosis, pulmonary fibrosis, and ischemic heart disease.

There are two different processes that result in scar. One is matrix accumulation, without matrix accumulation there is essentially no substance to form a scar. Scar formation can form with just excessive matrix deposition even without an inciting injury event. For instance, one TGF-beta model of glomerulonephritis in the kidney is based on excessive ECM accumulation that overwhelms the normal balance of matrix deposition and degradation. Another example is systemic sclerosis, a connective tissue disease characterized by fibrosis of the skin, subcutaneous tissue, and various internal organs due primarily to excessive accumulation of type I and III collagen. The other process that results in scar is lack of matrix organization.

Accordingly, there are two strategies to treat scar. One is decreasing matrix accumulation. The other is promoting matrix organization. However, reduction of scarring comprises more than the reduction of matrix accumulation. Arguably, the organization pattern of the accumulated matrix is more important than the amount of matrix present per se. This is supported by experimental evidence that neutralization of TGF-beta alone is wounds by anti-TGFbeta antibodies is not enough to eliminate scar. Thus, other mechanisms not related to TGF-beta mediated matrix accumulation are required for scarless repair.

Other known functions for the decorin family of proteoglycans include in vitro effect on collagen fibril formation. However, even in vitro, there are apparently different effects. For instance, decorin and FM interact with different sites on the collagen molecule. Meanwhile in vivo, SLRP knockout animals demonstrate different morphology indicating different functions and tissue distributions of the SLRPs in vivo. For instance, FM knockout mice have no discernable skin abnormalities and minimal FM has been detected in skin. FM, in contrast to decorin is not elevated during non-regenerative type repair.

Therefore the surprising and novel aspect of this is the surprising upregulation of FM during regenerative repair in the fetus and absence of FM during non-regenerative repair with scar. Even more surprising was the upregulation of decorin with non-regenerative repair in adult and late gestation animals. Moreover it was even more surprising that elimination of FM alone was enough to prevent organized collagen deposition and addition of FM alone was enough to promote organized collagen deposition in fetal animals.

Treatment of Intact or Non-Intact Skin to Decrease Inflammation

A novel aspect of this invention is that a heretofore unrecognized sequence of events in which modulation of decorin and biglycan can modulate TNF-α, a major inflammatory cytokine involved in multiple inflammatory skin conditions and modulation of corresponding dermatan sulfate moieties on decorin or biglycan can modulate leukocytosis, a major component of the inflammatory response. Thus, modulation of decorin, biglycan, and/or corresponding dermatan sulfate moieties can impact a myriad of inflammatory conditions associated with intact or non-intact skin. For instance, mild exposure to UV radiation (i.e., sunburn) and skin rubbing or scratching are examples of actions that can induce skin inflammation without a break in epidermal integrity (definition of intact skin). Other examples of inflammatory skin conditions that may be accompanied by intact or non-intact skin include, but are not limited to non-allergenic skin inflammatory conditions, allergic skin inflammatory conditions, neurogenic skin inflammatory conditions, UVR induced skin inflammatory conditions, or miscellaneous skin inflammatory conditions. Thus, a composition comprising one or more of SLRPs and/or enzymes to modulate GAGs such as dermatan sulfate can be used to treat inflammatory conditions of the skin. Preferred embodiments include decorin and/or chondroitinase B.

Treatment of Intact or Non-Intact Skin to Decrease Hyperpigmentation

A novel aspect of this invention is that a heretofore unrecognized sequence of events in which modulation of decorin and FM can modulate bFGF, a potent melanocyte mitogen and modulate TNF-alpha, a major inflammatory cytokine. Another novel aspect of this invention is that a heretofore unrecognized sequence of events in which modulation of corresponding dermatan sulfate moieties on decorin or biglycan can modulate leukocytosis, a major component of the inflammatory response as well as modulate bFGF activity.

While not wishing to be bound by any particular theory, modulation of bFGF activity by modulating decorin and/or FM levels or by modulating dermatan sulfate levels through use of enzymes such as chondroitinase B, can directly impact bFGF mediated melanocyte proliferation. In addition, modulation of bFGF activity will also modulate SCF activity, a potent inducer of melanocyte proliferation and melanin production. Moreover, epidermal injuries or irritation can initiate an inflammatory response that may also stimulate melanocytes with resultant hyperpigmentation or injure melanocytes with resultant melanocyte cell death and hypopigmentation. The ability to decrease inflammation by modulating TNF-alpha, may potentially diminish melanocyte stimulation or injury with correspondingly decreased potential for hyperpigmentation or hypopigmentation.

Although the ability of certain SLRPs, e.g., decorin, biglycan, and FM, to bind TGF-beta has been described in the prior art in the context of decreasing ECM accumulation in the kidney, TGF-beta has not been implicated in problems of excessive pigmentation. In fact, TGF-beta1 strongly inhibits normal melanocyte proliferation and DNA synthesis in vitro (Krasagakis K, et al., *Anticancer Res.* 14:2565-2571, 1994). In addition, hyperpigmentation is a process completely different from scar formation. Scar formation involves excessive accumulation of fibrous tissue manufactured by fibroblasts and occurs with dermal injury. Hyperpigmentation, in contrast, involves excessive production and deposition of the pigment melanin by melanocytes and can occur with or without actual skin injury. In cases associated with injury, there is usually an accompanying inflammatory component. In cases without actual disruption of skin integrity, an inflammatory component may or may not be present depending on the degree of UVR exposure. Thus, hyperpigmentation can occur with or without associated skin inflammation and with or without associated skin injury, while scar formation is associated prerequisitely with dermal injury One embodiment of the invention would be toward application to acne lesions and insect bites which can induce significant hyperpigmentation in certain ethnic groups such as Asians, Latinos, can blacks. Another embodiment of the invention would be application to inflammatory skin conditions with the potential for hyperpigmentation such as, but not limited to, non-allergenic skin inflammatory conditions, allergic skin inflammatory conditions, neurogenic skin inflammatory conditions, UVR induced skin inflammatory conditions, or miscellaneous skin inflammatory conditions.

C. Fibromodulin

In one aspect of the present invention, a composition comprising FM can be used to promote skin regeneration. FM, one of several components expressed by fetal tissue and a SLRP, dramatically improves the organization of dermal collagen in skin without evidence of skin irritation. Purified FM or FM enriched cellular extracts, when applied topically, improved the condition of skin without irritation. In fact, application of FM resulted in a significant reduction of skin inflammation and inflammatory cytokine expression. Although the use of FM has been described in the art for reducing dermal scarring associated with acute cutaneous injury (see, U.S. Pat. Nos. 5,654,270 and 5,510,328), the current state of the art fails to describe the novel, cosmetic skin care use of FM or functionally equivalent molecules for promoting the condition of non-scarred skin. In addition, the current state of the art also fails to describe the novel, cosmetic or pharmacological use of FM, or functionally equivalent molecules for decreasing skin inflammation and hyperpigmentation.

In a representative embodiment of the present invention, specific compounds expressed by fetal tissues such as FM can be isolated from native tissues (wild-type form) or from suitable expression vehicles such as bacteria or yeast (recombinant form-with or without modification of the coding region) and then formulated into cosmetic or non-cosmetic compositions to improve the condition of skin. Examples of specific compositions are described herein. The following are intended to clarify, but not limit the scope of the invention.

The FM useful for promoting skin regeneration can be wild-type or recombinant FM. Purified wild-type FM protein can be obtained from commercially available sources (Sigma-Aldrich Corp., St Louis, Mo.). Recombinant FM is obtained by cloning the FM cDNA, preferably human, into a suitable expression vector (e.g., plasmid, adenovirus). The cDNA for human FM is known in the art. (GenBank accession number X75546).

In one embodiment, the coding sequence of the recombinant FM cDNA may also be genetically modified prior to recombinant expression to enhance specific characteristics using techniques well known in the art. For example, site-specific mutagenesis can be used to increase the binding affinity of the protein to its receptors by using oligonucleotide primers. In addition, hydrophilic and secretory sequence such as Ig kappa-chain or histidine and GST tag sequences can be added to increase purification efficiency. The non-coding sequence of the recombinant FM cDNA may also be genetically modified to enhance specific characteristics using techniques well known in the art. For example, native mammalian promoters may not be efficient enough to produce large amount of proteins. In such a case, CMV and SV40 promoters can be inserted into mammalian systems to increase transcription efficiency. In addition, a SV40 or β-globin poly A sequence can be added to the 3' end to increase stability and protein production efficiency.

In another embodiment, FM may be isolated from non-genetically modified cells or genetically modified cells. Methods of cell and tissue culturing, as well as methods of obtaining cellular lysates or extracts, are well described in the art and may be performed by one of ordinary skill in the art (Refer to Pollard J W, Walker J M. *Basic cell culture protocols,* 2nd ed. Humana Press, Totowa, N.J., 1997 for more information). Cell culture media enriched with FM may be isolated and the resultant supernatant processed. Such processing are apparent to one of ordinary skill in the art and can include, but are not limited to, concentration of the supernatant, specific compound purification from the supernatant, sterilization of the supernatant. The methods should ensure optimal preservation of biologic activity of the compounds expressed by fetal tissues. Aseptic processing and other efforts to promote sterilization are also desirable.

Representative embodiments of the present invention may also contain, but are not limited to hyaluronic acid, ECM peptides or polypeptides, growth factors, L-ascorbic acid, or carbohydrate moieties such as lactose-1-phosphate, maltose-1-phosphate, mannose-6-phosphate, and lactose-6-phosphate. It is understood that the term hyaluronic acid includes its derivatives and broadly refers to naturally occurring, microbial and synthetic derivatives of acidic polysaccharides of various molecular weights constituted by residues of glucuronic acid and N-acetyl-D-glucosamine. Hyaluronic acid has been described as a skin conditioning agent for use in skin care compositions (see U.S. Pat. No. 6,444,647). It is also believed to play an important role in fetal tissue regeneration. (Burd D A, Greco R M, Regauer S, Longaker M T, Siebert J W, Garg H G. Hyaluronan and wound healing: a new perspective. *Br J Plast Surg* 44:579-84, 1991). Monosaccharide carbohydrate moieties such as lactose-1-phosphate, maltose-1-phosphate, mannose-6-phosphate, and lactose-6-phosphate have been described as being useful in preventing or minimizing inflammation (DiCorleto P E, and de la Motte C A., *J Immunol.* 143:3666-3672, 1989; Crestani B, et al., *Am J Physiol.* 264:L391-400, 1993; Bartlett M R, et al., *Immunol Cell Biol.* 72:367-374, 1994; Davis R H, et al., *J Am Podiatr Med Assoc.* 84:77-81, 1994).

In one representative embodiment of the present invention, hyaluronic acid is used with compounds expressed by fetal tissues for skin conditioning purposes and to potentiate the effects of cosmetic skin care compositions containing compounds expressed by fetal tissues. A representative skin care composition may comprise, for example, from about 0.1% to about 10% by weight of hyaluronic acid.

D. Dosages

The amount of the compounds expressed by fetal tissues included in the composition described herein varies with the skin conditions of a mammal. Generally, the compositions and ranges by weight depend on several factors including: the molecular weight of the compound(s), the purity of the compound(s), the bioactivity of the compound(s), and the degradation profile of the compound(s). For instance, enzymes, growth factors and cytokines, can be relatively small molecules. Hence they will exhibit relatively higher bioactivity for a given weight; however, growth factors and cytokines are also easily degraded in the absence of any protective delivery vehicles and thus, must be provided in higher dosages by weight for biological efficacy in circumstances lacking a delivery vehicle. In contrast other molecules such as collagens or proteoglycans that have potentially ECM structural functions are generally larger with potentially less bioactivity for a given molecular weight, and are more resistant to degradation. Thus, other molecules such as collagens or proteoglycans may be provided in higher or lower dosages by weight depending on the factors outlined above. In one embodiment, the composition may comprise about 0.0001% to about 10% by weight of the proteoglycan compound which is purified, and about 0.1% to about 80% by weight of a cell lysate, extract, or media enriched with the proteoglycan compound. In another embodiment, the composition may comprise about 0.0001% to about 10% by weight of the enzyme or growth factor compound which is purified, or of 0.000000001% to about 0.0001% by weight of the enzyme or growth factor compound which is purified, and about 0.1% to about 80% by weight of a cell lysate, extract, or media enriched with the enzyme or growth factor compound. In another embodiment, the composition may comprise about 0.001 IU/ml to about 1 IU/ml of the enzyme compound which is purified, or about IU/ml to about 1000 IU/ml of the enzyme compound which is purified.

E. Additional Skin Care Actives

The compositions of the present invention may contain a safe and effective amount of one or more additional skin care actives selected from, but not limited to, the group consisting of desquamatory actives, anti-acne actives, retinoids, hydroxy acids, peptides, polypeptides, growth factors, cytokines, anti-oxidants, radical scavengers, chelators, anti-inflammatory agents, topical anesthetics, tanning actives, skin lightening agents, anti-cellulite agents, flavonoids, anti-microbial actives, skin soothing agents, skin healing agents, antifungal actives, sunscreen actives, conditioning agents, structuring agents, thickening agents, and mixtures thereof. The amount of the additional skin care actives may vary with the specific skin conditions to be modulated. In one embodiment, the composition may contain from about 0.000001% to about 10% by weight of at least one additional skin care active.

In a representative embodiment, where the composition is to be in contact with human keratinous tissue, the additional components should be suitable for application to keratinous tissue, that is, when incorporated into the composition they are suitable for use in contact with human keratinous tissue without undue toxicity, incompatibility, instability, allergic response, and the like within the scope of sound medical judgment. The CTFA Cosmetic Ingredient Handbook, Second Edition (1992) describes a wide variety of nonlimiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials (e.g., polymers), for aiding the film-forming properties and substantivity of the composition (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, thickeners, and vitamins and derivatives thereof.

In any embodiment of the present invention, however, the actives useful herein can be categorized by the benefit they provide or by their postulated mode of action. However, it is to be understood that the actives useful herein can in some instances provide more than one benefit or operate via more than one mode of action. Therefore, classifications herein are made for the sake of convenience and are not intended to limit the active to that particular application or applications listed.

Desquamation Actives

A safe and effective amount of a desquamation active may be added to the compositions of the present invention, more preferably from about 0.1% to about 10%, even more preferably from about 0.2% to about 5%, also preferably from about 0.5% to about 4%, by weight of the composition.

Desquamation actives enhance the skin appearance benefits of the present invention. For example, the desquamation actives tend to improve the texture of the skin (e.g., smoothness). One desquamation system that is suitable for use herein contains sulfhydryl compounds and zwitterionic surfactants and is described in U.S. Pat. No. 5,681,852, to Bissett, incorporated herein by reference. Another desquamation system that is suitable for use herein contains salicylic acid and zwitterionic surfactants and is described in U.S. Pat. No. 5,652,228 to Bissett, incorporated herein by reference. Zwitterionic surfactants such as described in these applications are also useful as desquamatory agents herein, with cetyl betaine being particularly representative.

Anti-Acne Actives

The compositions of the present invention may contain a safe and effective amount of one or more anti-acne actives. Examples of useful anti-acne actives include resorcinol, sulfur, salicylic acid, benzoyl peroxide, erythromycin, zinc, etc. Further examples of suitable anti-acne actives are described in further detail in U.S. Pat. No. 5,607,980 to McAtee et. al.

Anti-Wrinkle Actives/Anti-Atrophy Actives

The compositions of the present invention may further contain a safe and effective amount of one or more anti-wrinkle actives or anti-atrophy actives. Exemplary anti-wrinkle/anti-atrophy actives suitable for use in the compositions of the present invention include sulfur-containing D and L amino acids and their derivatives and salts, particularly the N-acetyl derivatives, a representative example of which is N-acetyl-L-cysteine; thiols (e.g. ethane thiol); hydroxy acids (e.g., alpha-hydroxy acids such as lactic acid and glycolic acid or beta-hydroxy acids such as salicylic acid and salicylic acid derivatives such as the octanoyl derivative), phytic acid, lipoic acid; lysophosphatidic acid, skin peel agents (e.g., phenol and the like), and retinoids which enhance the keratinous tissue appearance benefits of the present invention, especially in regulating keratinous tissue condition (e.g., skin condition).

As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably retinol, retinol esters (e.g., $C_2$-$C_{22}$ alkyl esters of retinol, including retinyl palmitate, retinyl acetate, retinyl propionate), retinal, and/or retinoic acid (including all-trans-retinoic acid and/or 13-cis-retinoic acid), more preferably retinoids other than retinoic acid. These compounds are well known in the art and are commercially available from a number of sources (e.g., Sigma Chemical Company (St. Louis, Mo.), and Boerhinger Mannheim (Indianapolis, Ind.)). Other retinoids which are useful herein are described in U.S. Pat. No. 4,677,120 to Parish et al.; U.S. Pat. No. 4,885,311 to Parish et al.; U.S. Pat. No. 5,049,584 to Purcell et al.; U.S. Pat. No. 5,124,356 to Purcell et al.; and U.S. Pat. No. Reissue 34,075 to Purcell et al. Other suitable retinoids are tocopheryl-retinoate [tocopherol ester of retinoic acid (trans- or cis-), adapalene {6-[3-(1-adamantyl)-4-methoxyphenyl]-2-naphthoic acid}, and tazarotene (ethyl 6-[2-(4,4-dimethylthiochroman-6-yl)-ethynyl]nicotinate). Representative retinoids are retinol, retinyl palmitate, retinyl acetate, retinyl propionate, retinal and combinations thereof.

The compositions preferably contain from or about 0.005% to or about 2%, more preferably 0.01% to or about 2%, retinoid. Retinol is preferably used in an amount of from or about 0.01% to or about 0.15%; retinol esters are preferably used in an amount of from or about 0.01% to or about 2% (e.g., about 1%); retinoic acids are preferably used in an amount of from or about 0.01% to or about 0.25%; tocopheryl-retinoate, adapalene, and tazarotene are preferably used in an amount of from or about 0.01% to or about 2%.

Peptides/Polypeptides

As used herein, any naturally occurring, enzyme digested, or synthesized amino acid sequences of more than 3, but equal to or less than 34 amino acids is referred to as a "peptides", while "polypeptides" refers any naturally occurring, enzyme digested, or synthesized amino acid sequences of more than 34 amino acids.

Peptides, including but not limited to, di-, tri-, tetra-, and pentapeptides and derivatives thereof, as well as enzymatically cleaved fragments of ECM components such as collagen, elastins, may be included in the compositions of the present invention in amounts that are safe and effective. Also useful herein are naturally occurring and commercially available compositions that contain peptides.

When included in the present compositions, peptides are preferably included in amounts from about $1\times10^{-6}$% to about 10%, more preferably from about $1\times10^{-6}$% to about 0.1%, even more preferably from about $1\times10^{-5}$% to about 0.01%, by weight of the composition. In certain compositions where the peptide is CARNOSINE®, the compositions preferably contain from about 0.1% to about 5%, by weight of the composition, of such peptides.

Growth Factors/Cytokines

Although compounds expressed by fetal tissues may include growth factors and cytokines, representative embodiments of the present composition may also include a safe and effective amount of additional growth factors or cytokines not necessarily expressed by fetal tissues. Cell growth stimulating compounds or factors are herein described as natural or exogenous compounds which have a stimulating effect on the elaboration and growth of specific cell lines. These include anabolic growth hormones, such as human growth hormone and thyroid stimulating hormone, or on specific cell lines such as granulocytes, platelets or erythrocytes. Specifically, with regard to promoting epidermal growth, such as in skin tissue repair or wound healing, various factors have been identified as growth factors, including but not limited to: epidermal growth factor (EGF), fibroblast growth factor (FGF), transforming growth factor (TGF), vascular endothelial cell growth factor (VEGF), and insulin-like growth factor (IGF).

Anti-Oxidants/Radical Scavengers

The compositions of the present invention may include a safe and effective amount of an anti-oxidant/radical scavenger. The anti-oxidant/radical scavenger is especially useful for providing protection against UV radiation which can cause increased scaling or texture changes in the stratum corneum and against other environmental agents which can cause skin damage.

A safe and effective amount of an anti-oxidant/radical scavenger may be added to the compositions of the subject invention, preferably from about 0.1% to about 10%, more preferably from about 1% to about 5%, of the composition.

Anti-oxidants/radical scavengers such as ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethyl-chroman-2-carboxylic acid (commercially available under the tradename TROLOX®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts may be used. Representative anti-oxidants/radical scavengers are selected from tocopherol sorbate and other esters of tocopherol, more preferably tocopherol sorbate. For example, the use of tocopherol sorbate in topical compositions and applicable to the present invention is described in U.S. Pat. No. 4,847,071 to Donald L. Bissett, Rodney D. Bush and Ranjit Chatterjee.

Chelators

The compositions of the present invention may also contain a safe and effective amount of a chelator or chelating agent. As used herein, "chelator" or "chelating agent" means an active agent capable of removing a metal ion from a system by forming a complex so that the metal ion cannot readily participate in or catalyze chemical reactions. The inclusion of a chelating agent is especially useful for providing protection against UV radiation which can contribute to excessive scaling or skin texture changes and against other environmental agents which can cause skin damage.

A safe and effective amount of a chelating agent may be added to the compositions of the subject invention, preferably from about 0.1% to about 10%, more preferably from about 1% to about 5%, of the composition. Exemplary chelators that are useful herein are disclosed in U.S. Pat. No. 5,487,884 to Bissett et al.; PCT Publication No. WO91/16035, Bush et al.; and PCT Publication No. WO91/16034, Bush et al. Representative chelators useful in compositions of the subject invention are furildioxime, furilmonoxime, and derivatives thereof.

Flavonoids

The compositions of the present invention may optionally contain a flavonoid compound. Flavonoids are broadly disclosed in U.S. Pat. Nos. 5,686,082 and 5,686,367, both of which are herein incorporated by reference. Flavonoid compounds useful herein are commercially available from a number of sources, e.g., Indofine Chemical Company, Inc. (Somerville, N.J.), Steraloids, Inc. (Wilton, N.H.), and Aldrich Chemical Company, Inc. (Milwaukee, Wis.). Mixtures of the flavonoid compounds may also be used.

The herein described flavonoid compounds are preferably present in the instant invention at concentrations of from about 0.01% to about 20%, more preferably from about 0.1% to about 10%, and still more preferably from about 0.5% to about 5%.

Anti-Inflammatory Agents

A safe and effective amount of an anti-inflammatory agent may be added to the compositions of the present invention, preferably from about 0.1% to about 10%, more preferably from about 0.5% to about 5%, of the composition. The anti-inflammatory agent enhances the skin appearance benefits of the present invention, e.g., such agents contribute to a more uniform and acceptable skin tone or color. The exact amount of anti-inflammatory agent to be used in the compositions will depend on the particular anti-inflammatory agent utilized since such agents vary widely in potency.

Exemplary of anti-inflammatory agents are, but not limited to, steroidal anti-inflammatory and non-steroidal agents. The variety of compounds encompassed by these groups are well-known to those skilled in the art. For example, one may refer to standard texts for anti-inflammatory agents, including Rainsford K D (1985) Anti-inflammatory and anti-rheumatic drugs. CRC Press, Boca Raton, Fla. and Scherrer R A, Whitehouse M W (1974) Antiinflammatory agents; chemistry and pharmacology. Academic Press, New York.

In addition, natural or synthetic modulators of transforming growth factor beta, or other major inflammatory growth factors may also minimize inflammation when applied as a cosmetic product. (Logan A, Frautschy S A, Gonzalez A M, Sporn M B, Baird A. Enhanced expression of transforming growth factor beta 1 in the rat brain after a localized cerebral injury. *Brain Res* 587:216-25, 1992; Border W A, Noble N A, Yamamoto T, Harper J R, Yamaguchi Y, Pierschbacher M D, Ruoslahti E. Natural inhibitor of transforming growth factor-beta protects against scarring in experimental kidney disease. *Nature* 360:361-4, 1992).

In one embodiment, the so-called "natural" anti-inflammatory agents are useful in methods of the present invention. Such agents may suitably be obtained as an extract by suitable physical and/or chemical isolation from natural sources (e.g., plants, fungi, by-products of microorganisms) or can be synthetically prepared. For example, candelilla wax, bisabolol (e.g., alpha bisabolol), aloe vera, plant sterols (e.g., phytosterol), Manjistha (extracted from plants in the genus *Rubia*, particularly *Rubia Cordifolia*), and Guggal (extracted from plants in the genus *Commiphora*, particularly *Commiphora Mukul*), kola extract, chamomile, red clover extract, and sea whip extract, may be used.

Anti-Cellulite Agents

The compositions of the present invention may also contain a safe and effective amount of an anti-cellulite agent. Suitable agents may include, but are not limited to, xanthine compounds (e.g., caffeine, theophylline, theobromine, and aminophylline).

Topical Anesthetics

The compositions of the present invention may also contain a safe and effective amount of a topical anesthetic. Examples of topical anesthetic drugs include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

Tanning Actives

The compositions of the present invention may contain a tanning active. When present, it is preferable that the compositions contain from about 0.1% to about 20%, more preferably from about 2% to about 7%, and still more preferably from about 3% to about 6%, by weight of the composition, of dihydroxyacetone as an artificial tanning active.

Dihydroxyacetone, which is also known as DHA or 1,3-dihydroxy-2-propanone, is a white to off-white, crystalline powder.

The compound can exist as a mixture of monomers and dimers, with the dimers predominating in the solid crystalline state. Upon heating or melting, the dimers break down to yield the monomers. This conversion of the dimeric form to the monomeric form also occurs in aqueous solution. Dihydroxyacetone is also known to be more stable at acidic pH values. (See Windholz M, Merck & Co (1983) The Merck index: an encyclopedia of chemicals, drugs, and biologicals, 10th ed. Merck, Rahway, N.J., entry 3167, p. 463 and "Dihydroxyacetone for Cosmetics", E. Merck Technical Bulletin, 03-304 110, 319 897, 180 588.)

Skin Lightening Agents

The compositions of the present invention may contain a skin lightening agent. When used, the compositions preferably contain from about 0.1% to about 10%, more preferably from about 0.2% to about 5%, also preferably from about 0.5% to about 2%, by weight of the composition, of a skin lightening agent. Suitable skin lightening agents include those known in the art, including kojic acid, arbutin, ascorbic acid and derivatives thereof (e.g., magnesium ascorbyl phosphate or sodium ascorbyl phosphate), and extracts (e.g., mulberry extract, placental extract). Skin lightening agents suitable for use herein also include those described in PCT Publication No. WO95/34280, in the name of Hillebrand, corresponding to PCT Application No. U.S. WO95/07432, filed Jun. 12, 1995; and U.S. Pat. No. 6,068,834 filed in the names of Kvalnes, Mitchell A. DeLong, Barton J. Bradbury, Curtis B. Motley, and John D. Carter, corresponding to PCT Publication No. WO95/23780.

Skin Soothing and Skin Healing Actives

The compositions of the present invention may comprise a skin soothing or skin healing active. Skin soothing or skin healing actives suitable for use herein include panthenoic acid derivatives (including panthenol, dexpanthenol, ethyl panthenol), aloe vera, allantoin, bisabolol, and dipotassium glycyrrhizinate. A safe and effective amount of a skin soothing or skin healing active may be added to the present composition, preferably, from about 0.1% to about 30%, more preferably from about 0.5% to about 20%, still more preferably from about 0.5% to about 10%, by weight of the composition formed.

Antimicrobial and Antifungal Actives

The compositions of the present invention may contain an antimicrobial or antifungal active. Such actives are capable of destroying microbes, preventing the development of microbes or preventing the pathogenic action of microbes. A safe and effective amount of an antimicrobial or antifungal active may be added to the present compositions, preferably, from about 0.001% to about 10%, more preferably from about 0.01% to about 5%, and still more preferably from about 0.05% to about 2%.

Examples of antimicrobial and antifungal actives include B-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, ketaconazole, amanfadine hydrochloride, amanfadine sulfate, octopirox, parachlorometa xylenol, nystatin, tolnaftate, zinc pyrithione and clotrimazole.

Representative examples of actives useful herein include those selected from salicylic acid, benzoyl peroxide, 3-hydroxy benzoic acid, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, phytic acid, N-acetyl-L-cysteine, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, ketoconazole, neocycin sulfate, and mixtures thereof.

Sunscreen Actives

Exposure to ultraviolet light can result in excessive scaling and texture changes of the stratum corneum. Therefore, the compositions of the subject invention may optionally contain a sunscreen active. As used herein, "sunscreen active" includes both sunscreen agents and physical sunblocks. Suitable sunscreen actives may be organic or inorganic.

Inorganic sunscreens useful herein include the following metallic oxides; titanium dioxide having an average primary particle size of from about 15 nm to about 100 nm, zinc oxide having an average primary particle size of from about 15 nm to about 150 nm, zirconium oxide having an average primary particle size of from about 15 nm to about 150 nm, iron oxide having an average primary particle size of from about 15 nm to about 500 nm, and mixtures thereof. When used herein, the inorganic sunscreens are present in the amount of from about 0.1% to about 20%, preferably from about 0.5% to about 10%, more preferably from about 1% to about 5%, by weight of the composition.

A wide variety of conventional organic sunscreen actives are suitable for use herein. Balsam M S, Sagarin E (1972) Cosmetics, Science and Technology, 2d edn. Wiley-Interscience, New York, discloses numerous suitable actives.

More representative organic sunscreen actives useful in the compositions useful in the subject invention are 2-ethylhexyl-p-methoxycinnamate, butylmethoxydibenzoylmethane, 2-hydroxy-4-methoxybenzo-phenone, 2-phenylbenzimidazole-5-sulfonic acid, octyldimethyl-p-aminobenzoic acid, octocrylene and mixtures thereof.

Also particularly useful in the compositions are sunscreen actives such as those disclosed in U.S. Pat. No. 4,937,370 to Sabatelli and U.S. Pat. No. 4,999,186 to Sabatelli & Spirnak. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Representative members of this class of sunscreening agents are 4-N,N-(2-ethylhexyl)methyl-aminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl)methyl-aminobenzoic acid ester with 4-hydroxydibenzoylmethane; 4-N,N-(2-ethylhexyl)methyl-aminobenzoic acid ester of 2-hydroxy-4-(2-hydroxyethoxy)benzophenone; 4-N,N-(2-ethylhexyl)-methylaminobenzoic acid ester of 4-(2-hydroxyethoxy)dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy)dibenzoylmethane and mixtures thereof.

Especially representative sunscreen actives include 4,4'-t-butylmethoxydibenzoylmethane, 2-ethylhexyl-p-methoxycinnamate, phenyl benzimidazole sulfonic acid, and octocrylene.

A safe and effective amount of the organic sunscreen active is used, typically from about 1% to about 20%, more typically from about 2% to about 10% by weight of the composition. Exact amounts will vary depending upon the sunscreen or sunscreens chosen and the desired Sun Protection Factor ("SPF").

Particulate Material

The compositions of the present invention may contain a particulate material, preferably a metallic oxide. These particulates can be coated or uncoated, charged or uncharged. Charged particulate materials are disclosed in U.S. Pat. No. 5,997,887 to Ha, et al., which is incorporated herein by reference. Particulate materials useful herein include; bismuth oxychloride, iron oxide, mica, mica treated with barium sulfate and $TiO_2$, silica, nylon, polyethylene, talc, styrene, polypropylene, ethylene/acrylic acid copolymer, sericite, titanium dioxide, bismuth oxychloride, iron oxide, aluminum oxide, silicone resin, barium sulfate, calcium carbonate, cellulose acetate, polymethyl methacrylate, and mixtures thereof.

Inorganic particulate materials (e.g., $TiO_2$, ZnO, or $ZrO_2$) are commercially available from a number of sources. One example of a suitable particulate material contains the material available from U.S. Cosmetics (TRONOX $TiO_2$ series, SAT-T CR837, a rutile $TiO_2$). Preferably, particulate materials are present in the composition in levels of from about 0.01% to about 2%, more preferably from about 0.05% to about 1.5%, still more preferably from about 0.1% to about 1%, by weight of the composition.

Conditioning Agents

The compositions of the present invention may contain a conditioning agent selected from humectants, moisturizers, or skin conditioners. A variety of these materials can be employed and each can be present at a level of from about 0.01% to about 20%, more preferably from about 0.1% to about 10%, and still more preferably from about 0.5% to about 7% by weight of the composition. These materials include, but are not limited to, guanidine; urea; glycolic acid and glycolate salts (e.g. ammonium and quaternary alkyl ammonium); salicylic acid; lactic acid and lactate salts (e.g., ammonium and quaternary alkyl ammonium); aloe vera in any of its variety of forms (e.g., aloe vera gel); polyhydroxy alcohols such as sorbitol, mannitol, xylitol, erythritol, glycerol, hexanetriol, butanetriol, propylene glycol, butylene glycol, hexylene glycol and the like; polyethylene glycols; sugars (e.g., melibiose) and starches; sugar and starch derivatives (e.g., alkoxylated glucose, fucose, glucosamine); hyaluronic acid; lactamide monoethanolamine; acetamide monoethanolamine; panthenol; allantoin; and mixtures thereof. Also useful herein are the propoxylated glycerols described in U.S. Pat. No. 4,976,953 to Orr et al.

Also useful are various $C_1$-$C_{30}$ monoesters and polyesters of sugars and related materials. These esters are derived from a sugar or polyol moiety and one or more carboxylic acid moieties. Such ester materials are further described in, U.S. Pat. Nos. 2,831,854, 4,005,196, to Jandacek; U.S. Pat. No. 4,005,195 to Jandacek; U.S. Pat. No. 5,306,516 to Letton et al.; U.S. Pat. No. 5,306,515 to Letton et al.; U.S. Pat. No. 5,305,514 to Letton et al.; U.S. Pat. No. 4,797,300 to Jandacek et al.; U.S. Pat. No. 3,963,699 to Rizzi et al.; U.S. Pat. No. 4,518,772 to Volpenhein; and U.S. Pat. No. 4,517,360 to Volpenhein.

Structuring Agents

In one embodiment, the compositions hereof, and especially the emulsions hereof, may contain a structuring agent. Structuring agents are particularly representative in the oil-in-water emulsions of the present invention. Without being limited by theory, it is believed that the structuring agent assists in providing rheological characteristics to the composition which contribute to the stability of the composition. For example, the structuring agent tends to assist in the formation of the liquid crystalline gel network structures. The structuring agent may also function as an emulsifier or surfactant. Representative compositions of this invention contain from about 0.1% to about 20%, more preferably from about 0.1% to about 10%, still more preferably from about 0.5% to about 9%, of one or more structuring agents.

Representative structuring agents are those having an HLB of from about 1 to about 8 and having a melting point of at least about 45° C. Suitable structuring agents are those selected from saturated $C_{14}$-$C_{30}$ fatty alcohols, saturated $C_{16}$-$C_{30}$ fatty alcohols containing from about 1 to about 5 moles of ethylene oxide, saturated $C_{16}$-$C_{30}$ diols, saturated $C_{16}$-$C_{30}$ monoglycerol ethers, saturated $C_{16}$-$C_{30}$ hydroxy fatty acids, $C_{14}$-$C_{30}$ hydroxylated and nonhydroxylated saturated fatty acids, $C_{14}$-$C_{30}$ saturated ethoxylated fatty acids, amines and alcohols containing from about 1 to about 5 moles of ethylene oxide diols, $C_{14}$-$C_{30}$ saturated glyceryl mono esters with a monoglyceride content of at least 40%, $C_{14}$-$C_{30}$ saturated polyglycerol esters having from about 1 to about 3 alkyl group and from about 2 to about 3 saturated glycerol units, $C_{14}$-$C_{30}$ glyceryl mono ethers, $C_{14}$-$C_{30}$ sorbitan mono/diesters, $C_{14}$-$C_{30}$ saturated ethoxylated sorbitan mono/diesters with about 1 to about 5 moles of ethylene oxide, $C_{14}$-$C_{30}$ saturated methyl glucoside esters, $C_{14}$-$C_{30}$ saturated sucrose mono/diesters, $C_{14}$-$C_{30}$ saturated ethoxylated methyl glucoside esters with about 1 to about 5 moles of ethylene oxide, $C_{14}$-$C_{30}$ saturated polyglucosides having an average of between 1 to 2 glucose units and mixtures thereof, having a melting point of at least about 45° C.

Some representative structuring agents of the present invention are selected from stearic acid, palmitic acid, stearyl alcohol, cetyl alcohol, behenyl alcohol, stearic acid, palmitic acid, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof. More representative structuring agents of the present invention are selected from stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof. Even more representative structuring agents are selected from stearic acid, palmitic acid, stearyl alcohol, cetyl alcohol, behenyl alcohol, steareth-2, and mixtures thereof.

Thickening Agent (Including Thickeners and Gelling Agents)

In one embodiment, the compositions of the present invention can contain one or more thickening agents, preferably from about 0.1% to about 5%, more preferably from about 0.1% to about 4%, and still more preferably from about 0.25% to about 3%, by weight of the composition.

Nonlimiting classes of thickening agents include those selected from the following: carboxylic acid polymers, crosslinked polyacrylate polymers, polyacrylamide polymers, polysaccharides, and gelling agent gums.

Carboxylic acid polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Polymers useful in the present invention are more fully described in U.S. Pat. No. 5,087,445, to Haffey et al.; U.S. Pat. No. 4,509,949 to Huang et al; U.S. Pat. No. 2,798,053 to Brown; and in Wenninger J A, McEwen G N, Cosmetic Toiletry and Fragrance Association (1993) International cosmetic ingredient dictionary, 5th ed. Cosmetic Toiletry and Fragrance Association, Washington, D.C.

Crosslinked polyacrylate polymers are useful as thickeners or gelling agents including both cationic and nonionic polymers, with the cationics being generally representative. Examples of useful crosslinked nonionic polyacrylate polymers and crosslinked cationic polyacrylate polymers are those described in U.S. Pat. No. 5,100,660 to Hawe et al.; U.S. Pat. No. 4,849,484 to Heard; U.S. Pat. No. 4,835,206 to Farrar et al.; U.S. Pat. No. 4,628,078 to Glover et al.; U.S. Pat. No. 4,599,379 to Flesher et al.; and EP 228,868 to Farrar et al.

Polyacrylamide polymers, especially nonionic polyacrylamide polymers including substituted branched or unbranched polymers. More representative among these polyacrylamide polymers is the nonionic polymer given the CTFA designation polyacrylamide and isoparaffin and laureth-7, available under the Tradename Sepigel 305 from Seppic Corporation (Fairfield, N.J.). Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, and SSSA100H, from Lipo Chemicals, Inc., (Patterson, N.J.).

"Polysaccharides" refer to gelling agents which contain a backbone of repeating sugar (i.e., carbohydrate) units. Nonlimiting examples of polysaccharide gelling agents include those selected from cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. In these polymers, the hydroxy groups of the cellulose polymer is hydroxyalkylated (preferably hydroxyethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Examples of alkyl groups useful herein include those selected from stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof. Representative among the alkyl hydroxyalkyl cellulose ethers is the material given the CTFA designation cetyl hydroxyethylcellulose, which is the ether of cetyl alcohol and hydroxyethylcellulose. This material is sold under the tradename NATROSOL® CS Plus from Aqualon Corporation (Wilmington, Del.). Other useful polysaccharides include scleroglucans which are a linear chain of (1-3) linked glucose units with a (1-6) linked glucose every three units, a commercially available example of which is CLEAROGEL® CS11 from Michel Mercier Products Inc. (Mountainside, N.J.).

Other thickening and gelling agents useful herein include materials which are primarily derived from natural sources. Nonlimiting examples of these gelling agent gums include acacia, agar, align, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

Additional Actives

The compositions of the present invention can contain additional skin care actives not comprising a specific category include, but are not limited to a safe and effective amount of farnesol and phytantrriol.

Farnesol is a naturally occurring substance which is believed to act as a precursor and/or intermediate in the biosynthesis of squalene and sterols, especially cholesterol. Farnesol is also involved in protein modification and regulation (e.g., farnesylation of proteins), and there is a cell nuclear receptor which is responsive to farnesol.

Chemically, framesol is 3,7,11-trimethyl-2,6,10-dodecatrien-1-ol and as used herein "framesol" includes isomers and tautomers of such. Farnesol is commercially available, e.g., under the names farnesol (a mixture of isomers from Dragoco, 10 Gordon Drive, Totowa, N.J.) and trans-trans-farnesol (Sigma Chemical Company, P.O. Box 14508, St. Louis, Mo.).

When present in the compositions of the present invention, the composition preferably contains from about 0.001% to about 50%, by weight of the composition, more preferably from about 0.01% to about 20%, even more preferably from about 0.1% to about 15%, even more preferably from about 0.1% to about 10%, still more preferably from about 0.5% to about 5%, and still more preferably from about 1% to about 5% of farnesol.

Phytantriol is the common name for the chemical known as 3,7,11,15,tetramethylhexadecane-1,2,3,-triol. Phytantriol is commercially available from BASF (1609 Biddle Avenue, Whyandotte, Mich.). For example, phytantriol is useful as a spider vessel/red blotchiness repair agent, a dark circle/puffy eye repair agent, sallowness repair agent, a sagging repair agent, an anti-itch agent, a skin thickening agent, a pore reduction agent, oil/shine reduction agent, a post-inflammatory hyperpigmentation repair agent, wound treating agent, an anti-cellulite agent, and regulating skin texture, including wrinkles and fine lines.

In the compositions of the present invention, the phytantriol preferably is included in an amount from about 0.001% to about 50% by weight of the composition, more preferably from about 0.01% to about 20%, even more preferably from about 0.1% to about 15%, even more preferably from about 0.2% to about 10%, still more preferably from about 0.5% to about 10%, and still more preferably from about 1% to about 5%.

F. Cosmetically, Dermatologically or Pharmaceutically Acceptable Carriers

The composition provided herein may optionally include a cosmetically acceptable, dermatologically acceptable, or pharmaceutically acceptable carriers. Cosmetically acceptable, dermatologically acceptable, or pharmaceutically acceptable carriers are well known in the art (Shai A, et al. Principles of preparation of medical and cosmetic products. *Handbook of Cosmetic Skin Care*. London: Martin Dunitz Ltd., pp. 19-31, 2001).

In one embodiment, the topical compositions of the present invention also have a dermatologically acceptable carrier. A safe and effective amount of carrier is from about 50% to about 99.99%, preferably from about 80% to about 99.9%, more preferably from about 90% to about 98%, and even more preferably from about 90% to about 95% of the composition.

The carrier can be in a wide variety of forms. For example, emulsion carriers, including, but not limited to, oil-in-water, water-in-oil, water-in-oil-in-water, and oil-in-water-in-silicone emulsions, are useful herein.

Emulsions according to the present invention generally contain a solution as described above and a lipid or oil. Lipids and oils may be derived from animals, plants, or petroleum and may be natural or synthetic (i.e., man-made). Representative emulsions also contain a humectant, such as glycerin. Emulsions will preferably further contain from about 0.01% to about 10%, more preferably from about 0.1% to about 5%, of an emulsifier, based on the weight of the carrier. Emulsifiers may be nonionic, anionic or cationic. Suitable emulsifiers are disclosed in, for example, U.S. Pat. No. 3,755,560 to Dickert et al.; U.S. Pat. No. 4,421,769 to Dixon et al; and McCutcheon's Detergents and Emulsifiers, North American Edition, pages 317-324 (1986).

The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending on the desired product form. Exemplary low viscosity emulsions, which are representative, have a viscosity of about 50 centistokes or less, more preferably about 10 centistokes or less, still more preferably about 5 centistokes or less.

The compositions useful for the methods of the present invention are generally prepared by conventional methods such as are known in the art of making topical compositions. Such methods typically involve mixing of the ingredients in one or more steps to a relatively uniform state, with or without heating, cooling, application of vacuum, and the like.

G. Vesicular Delivery Systems

The major obstacle for topical drug delivery is the low diffusion rate of drugs across the stratum corneum. The natural function of the skin is to protect the body for unwanted influences from the environment. The main barrier of the skin is located in the outermost layer of the skin, the stratum corneum. Since the lipids regions in the stratum corneum form the only continuous structure, substances applied onto the skin always have to pass these regions. In order to increase transport across the skin, various vesicular delivery systems such as gel-state, liquid-state, and elastic vesicles have been described (Reviewed in Verma D D, et al., *Eur J Pharm Biopharm*. 55:271-277, 2003; Verma D D, et al., *Int J Pharm*. 258:141-151, 2003; Miyazaki S, et al., *J Pharm Pharm Sci*. 6:238-245, 2003; Takahashi A, et al., *Int J Pharm*. 246:179-186, 2002; Barry B W., *Adv Drug Deliv Rev*. 54 Suppl 1:S31-40, 2002; Barry B W., *Eur J Pharm Sci*. 14:101-114, 2001; Jain S, et al., *Drug Dev Ind Pharm*. 29:1013-1026, 2003).

IV. Methods of Using Compositions for Regulating Skin Condition

The compositions of the present invention are useful for promoting mammalian skin condition. Such regulation of keratinous tissue conditions can include prophylactic and therapeutic regulation. For example, such regulating methods are directed to thickening keratinous tissue (i.e., building the epidermis and/or dermis layers of the skin and where applicable the keratinous layers of the nail and hair shaft) and preventing and/or retarding atrophy of mammalian skin, preventing and/or retarding the appearance of spider vessels and/or red blotchiness on mammalian skin, preventing and/or retarding the appearance of dark circles under the eye of a mammal, preventing and/or retarding sallowness of mammalian skin, preventing and/or retarding sagging of mammalian skin, softening and/or smoothing lips, hair and nails of a mammal, preventing and/or relieving itch of mammalian skin, regulating skin texture (e.g. wrinkles and fine lines), and improving skin color (e.g. redness, freckles).

Regulating keratinous tissue condition involves topically applying to the keratinous tissue a safe and effective amount of a composition of the present invention. The amount of the composition which is applied, the frequency of application and the period of use will vary widely depending upon the fetal compounds and skin care active and/or other components of a given composition and the level of regulation desired (e.g., in light of the level of keratinous tissue damage present or expected to occur).

In a representative embodiment, the composition is chronically applied to the skin. By "chronic topical application", this means continued topical application of the composition over an extended period during the subject's lifetime, preferably for a period of at least about one week, more preferably for a period of at least about one month, even more preferably for at least about three months, even more preferably for at least about six months, and more preferably still for at least about one year. While benefits are obtainable after various maximum periods of use (e.g., five, ten or twenty years), it is representative that chronic application continue throughout the subject's lifetime. Typically applications would be on the order of about once per day over such extended periods, however application rates can vary from about once per week up to about three times per day or more.

A wide range of quantities of the compositions of the present invention can be employed to provide a skin appearance and/or feel benefit. Quantities of the present compositions which are typically applied per application are, in mg composition/cm$^2$ skin, from about 0.1 mg/cm$^2$ to about 10 mg/cm$^2$. A particularly useful application amount is about 1 mg/cm$^2$ to about 2 mg/cm$^2$.

Regulating keratinous tissue condition is preferably practiced by applying a composition in the form of a skin lotion, cream, gel, foam, ointment, paste, emulsion, spray, conditioner, tonic, cosmetic, lipstick, foundation, nail polish, after-shave, or the like which is preferably intended to be left on the skin or other keratin structure for some esthetic, prophylactic, therapeutic or other benefit (i.e., a "leave-on" composition). After applying the composition to the skin, it is preferably left on the skin for a period of at least about 15 minutes, more preferably at least about 30 minutes, even more preferably at least about 1 hour, still more preferably for at least several hours, e.g., up to about 12 hours. Any part of the external portion of the face, hair, and/or nails can be treated, e.g., face, lips, under-eye area, eyelids, scalp, neck, torso, arms, hands, legs, feet, fingernails, toenails, scalp hair, eyelashes, eyebrows, etc. The composition can be applied with the fingers or with an implement or device (e.g., pad, cotton ball, applicator pen, spray applicator, and the like).

Another approach to ensure a continuous exposure of the skin to at least a minimum level of fetal compounds and skin care actives is to apply the compound by use of a patch applied. Such an approach is particularly useful for problem skin areas needing more intensive treatment (e.g., facial crows feet area, frown lines, under eye area, and the like). The patch can be occlusive, semi-occlusive or non-occlusive and can be adhesive or non-adhesive. The composition can be contained within the patch or be applied to the skin prior to application of the patch. The patch can also include additional actives such as chemical initiators for exothermic reactions such as those described in U.S. Pat. Nos. 5,821, 250, 5,981,547, and 5,972,957 to Wu, et al. The patch is preferably left on the skin for a period of at least about 5 minutes, more preferably at least about 15 minutes, more preferably still at least about 30 minutes, even more preferably at least about 1 hour, still more preferably at night as a form of night therapy.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

In one embodiment, compounds expressed by fetal cells or tissues are isolated directly through tissue culture media or cell lysates and further concentrated or purified. Although individual identification or purification of compounds expressed by fetal tissues is useful, the application of this invention does not necessarily require the individual identification or purification of the compounds. The tissue culture media or cell lysate, with or without further concentration or purification, is then formulated into cosmetic compositions to improve the condition of skin according to the examples below.

In another embodiment of the present invention, compounds expressed by fetal tissues or conditions that promote expression of these compounds are identified. Once identified, the fetal compounds are isolated from native tissues (wild-type form) or from suitable expression vehicles such as bacteria or yeast (recombinant form-with or without modification of the coding region) and formulated into cosmetic compositions to improve the condition of skin according to the examples below.

The ingredient "Fetal Tissue Compounds" listed in the table below refers to, but is not necessarily limited to, fetal tissue culture media, lysates, and extracts that may or may not have undergone prior identification of each individual component. "Fetal Tissue Compounds" also refer to compounds directly derived from fetal tissues or compounds obtained through recombinant means with or without prior genetic modification.

TABLE 1

Examples of Skin Care Compositions Using Fetal Tissue Compounds

| Ingredient | Ex. 1 | Ex. 2 | Ex. 3 | Ex. 4 | Ex. 5 | Ex. 6 |
|---|---|---|---|---|---|---|
| PHASE A: | | | | | | |
| Water U.S.P. | qs to 100 | qs to 100 | qs to 100 | qs to 100 | Qs to 100 | qs to 100 |
| Disodium EDTA | 0.15 | 0.15 | 0.15 | 0.15 | 0.15 | 0.15 |
| Methyl Paraben | 0.25 | 0.25 | 0.25 | 0.25 | 0.25 | 0.25 |
| Allantoin | 0.20 | 0.20 | 0.20 | 0.20 | 0.20 | 0.20 |
| Glycerin | 5.0 | 5.0 | 5.0 | 5.0 | 5.0 | 5.0 |
| PHASE B: | | | | | | |
| Cetyl Alcohol | 0.30 | 0.30 | 0.30 | 0.30 | 0.30 | 0.30 |
| Stearyl Alcohol | 0.50 | 0.50 | 0.50 | 0.50 | 0.50 | 0.50 |
| Behenyl Alcohol | 0.40 | 0.40 | 0.40 | 0.40 | 0.40 | 0.40 |
| Propyl Paraben | 0.10 | 0.10 | 0.10 | 0.10 | 0.10 | 0.10 |
| Farnesol | 5.0 | 5.0 | 5.0 | 5.0 | 5.0 | 5.0 |
| Phytantriol | 5.0 | 5.0 | 5.0 | 5.0 | 5.0 | 5.0 |

TABLE 1-continued

Examples of Skin Care Compositions Using Fetal Tissue Compounds

| Ingredient | Ex. 1 | Ex. 2 | Ex. 3 | Ex. 4 | Ex. 5 | Ex. 6 |
|---|---|---|---|---|---|---|
| PHASE C | | | | | | |
| Sepigel 305 | 2.0 | 2.0 | 2.0 | 2.0 | 2.0 | 2.0 |
| PHASE D | | | | | | |
| Titanium Dioxide | | | | | | 0.5 |
| PHASE E | | | | | | |
| Benzyl Alcohol | 0.50 | 0.50 | 0.50 | 0.50 | 0.50 | 0.50 |
| Dimethicone/ Dimethiconol | 0.50 | 0.50 | 0.50 | 0.50 | 0.50 | 0.50 |
| PHASE F | | | | | | |
| Sodium Hyaluronate | 0.15 | 0.30 | 0.30 | 0.60 | 0.60 | 0.60 |
| Ascorbic Acid | 5.0 | 5.0 | 5.0 | 5.0 | 5.0 | 5.0 |
| PHASE G | | | | | | |
| Fetal Tissue Compounds | 5.0 | 10.0 | 20.0 | 30.0 | 45.0 | 60.0 |

To obtain a suitable skin composition, the Phase A components listed in the table above are blended with a suitable mixer (e.g., Tekmar model RW20DZM). The components are heated, while stirring to a temperature of 70-80° C. Separately, the B phase components are blended with a suitable mixer and heated to 70-75° C. and maintained while mixing. Phase B components are added to Phase A components while mixing well to emulsify. When the emulsion is at approximately 60° C., Phase C component is added while continuing to mix emulsion. The emulsion is allowed to cool to approximately 40° C. while stirring. At approximately 50° C., Phase D and E components are added to the emulsion and mixing continued. At approximately 40° C. Phase F components are added while continuing to mix emulsion. The emulsion is allowed to cool to approximately 30° C. while stirring, and Phase G component is added. The emulsion is then milled using a suitable mill (Tekmar T-25) for approximately 5 minutes resulting in a uniform product.

In yet another embodiment of the present invention, specific compounds expressed by fetal tissues such as FM are isolated from native tissues (wild-type form) or from suitable expression vehicles such as bacteria, yeast, or mammalian cells (recombinant form-with or without modification of the coding region) and then formulated into cosmetic compositions to improve the condition of skin according to the table and steps below. For example, wild-type or recombinant FM can be in either purified or partially purified or non-purified forms. Purified is understood to mean the presence of primarily FM protein. Partially or non-purified forms of FM may also contain other fetal compounds in the form of, but not limited to media, lysates, or extracts that improve the condition of skin.

A composition using purified FM and the following ingredients is prepared in making a reparative creme.

TABLE 2

Examples of Skin Care Compositions Using Purified FM

| Ingredient | Ex. 1 | Ex. 2 | Ex. 3 | Ex. 4 | Ex. 5 | Ex. 6 |
|---|---|---|---|---|---|---|
| PHASE A: | | | | | | |
| Water U.S.P. | qs to 100 | qs to 100 | qs to 100 | qs to 100 | qs to 100 | Qs to 100 |
| Disodium EDTA | 0.15 | 0.15 | 0.15 | 0.15 | 0.15 | 0.15 |
| Methyl Paraben | 0.25 | 0.25 | 0.25 | 0.25 | 0.25 | 0.25 |
| Allantoin | 0.20 | 0.20 | 0.20 | 0.20 | 0.20 | 0.20 |
| Glycerin | 5.0 | 5.0 | 5.0 | 5.0 | 5.0 | 5.0 |
| PHASE B: | | | | | | |
| Cetyl Alcohol | 0.30 | 0.30 | 0.30 | 0.30 | 0.30 | 0.30 |
| Stearyl Alcohol | 0.50 | 0.50 | 0.50 | 0.50 | 0.50 | 0.50 |
| Behenyl Alcohol | 0.40 | 0.40 | 0.40 | 0.40 | 0.40 | 0.40 |
| Propyl Paraben | 0.10 | 0.10 | 0.10 | 0.10 | 0.10 | 0.10 |
| Farnesol | 5.0 | 5.0 | 5.0 | 5.0 | 5.0 | 5.0 |
| Phytantriol | 5.0 | 5.0 | 5.0 | 5.0 | 5.0 | 5.0 |
| PHASE C | | | | | | |
| Sepigel 305 | 2.0 | 2.0 | 2.0 | 2.0 | 2.0 | 2.0 |
| PHASE D | | | | | | |
| Titanium Dioxide | | | | | | 0.5 |

TABLE 2-continued

Examples of Skin Care Compositions Using Purified FM

| Ingredient | Ex. 1 | Ex. 2 | Ex. 3 | Ex. 4 | Ex. 5 | Ex. 6 |
|---|---|---|---|---|---|---|
| PHASE E | | | | | | |
| Benzyl Alcohol | 0.50 | 0.50 | 0.50 | 0.50 | 0.50 | 0.50 |
| Dimethicone/ Dimethiconol | 0.50 | 0.50 | 0.50 | 0.50 | 0.50 | 0.50 |
| PHASE F | | | | | | |
| Sodium Hyaluronate | 0.15 | 0.30 | 0.30 | 0.60 | 0.60 | 0.60 |
| Ascorbic Acid | 5.0 | 5.0 | 5.0 | 5.0 | 5.0 | 5.0 |
| PHASE G | | | | | | |
| Purified FM | 0.001 | 0.01 | 0.1 | 1 | 5 | 10 |

The A phase components are blended with a suitable mixer (e.g., Tekmar model RW20DZM). Phase A components are heated while stirring to a temperature of 70-80° C. Separately, the B phase components are blended with a suitable mixer, heated to 70-75° C. and maintained while mixing. Phase B components are added to Phase A components while mixing well to emulsify. When emulsion is at approximately 60° C., Phase C components is added while continuing to mix emulsion. The emulsion is allowed to cool to approximately 40° C. while stirring. At approximately 50° C., Phase D and E components are added to the emulsion and mixing continued. At approximately 40° C. Phase F components is added while continuing to mix emulsion. The emulsion is allowed to cool to approximately 30° C. while stirring, and Phase G component is then added. The emulsion is then milled using a suitable mill (Tekmar T-25) for approx. 5 minutes resulting in an uniform product.

Alternatively, composition using partially or non-purified FM enriched lysates, extracts, or media, and the following ingredients are prepared in making a reparative crème using the ingredients below and the same steps described previously.

TABLE 3

Examples of Skin Care Compositions Using Partially or Non-Purified FM

| Ingredient | Ex. 1 | Ex. 2 | Ex. 3 | Ex. 4 | Ex. 5 | Ex. 6 |
|---|---|---|---|---|---|---|
| PHASE A: | | | | | | |
| Water U.S.P. | qs to 100 | qs to 100 | qs to 100 | qs to 100 | qs to 100 | Qs to 100 |
| Disodium EDTA | 0.15 | 0.15 | 0.15 | 0.15 | 0.15 | 0.15 |
| Methyl Paraben | 0.25 | 0.25 | 0.25 | 0.25 | 0.25 | 0.25 |
| Allantoin | 0.20 | 0.20 | 0.20 | 0.20 | 0.20 | 0.20 |
| Glycerin | 5.0 | 5.0 | 5.0 | 5.0 | 5.0 | 2.5 |
| PHASE B: | | | | | | |
| Cetyl alcohol | 0.30 | 0.30 | 0.30 | 0.30 | 0.30 | 0.30 |
| Stearyl alcohol | 0.50 | 0.50 | 0.50 | 0.50 | 0.50 | 0.50 |
| Behenyl alcohol | 0.40 | 0.40 | 0.40 | 0.40 | 0.40 | 0.40 |
| Propyl Paraben | 0.10 | 0.10 | 0.10 | 0.10 | 0.10 | 0.10 |
| Farnesol | 5.0 | 5.0 | 5.0 | 5.0 | 5.0 | 2.5 |
| Phytantriol | 5.0 | 5.0 | 5.0 | 5.0 | 5.0 | 2.5 |
| PHASE C: | | | | | | |
|  | 2.0 | 2.0 | 2.0 | 2.0 | 2.0 | 2.0 |
| PHASE D: | | | | | | |
| Titanium Dioxide | | | | | | 0.5 |

TABLE 3-continued

Examples of Skin Care Compositions Using Partially or Non-Purified FM

| Ingredient | Ex. 1 | Ex. 2 | Ex. 3 | Ex. 4 | Ex. 5 | Ex. 6 |
|---|---|---|---|---|---|---|
| PHASE E: | | | | | | |
| Benzyl alcohol | 0.50 | 0.50 | 0.50 | 0.50 | 0.50 | 0.50 |
| Dimethicone/ Dimethiconol | 0.50 | 0.50 | 0.50 | 0.50 | 0.50 | 0.50 |
| PHASE F: | | | | | | |
| Sodium hyaluronate | 0.15 | 0.30 | 0.30 | 0.60 | 0.60 | 0.60 |
| Ascorbic acid | 5.0 | 5.0 | 5.0 | 5.0 | 5.0 | — |
| PHASE G: | | | | | | |
| FM Enriched Lysates, Extracts, or Media | 0.1 | 1 | 10 | 20 | 40 | 80 |

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. The following claims are, therefore, to be read to include not only the combination of elements which are literally set forth, but all equivalent elements for performing substantially the same function in substantially the same way to obtain substantially the same result. The claims are thus to be understood to include what is specifically illustrated and described above, what is conceptually equivalent, and also what essentially incorporates the essence of the invention.

What is claimed is:

1. A method of modulating a skin condition of intact human skin, comprising:
    administering to the intact skin of a human being a composition comprising an effective amount of a compound to modulate the level of one selected from the group consisting of fibromodulin (FM), lumican, biglycan, and combinations thereof, alone or in combination with keratan sulfate, wherein the compound is selected from the group consisting of fibromodulin (FM), lumican, biglycan, and combinations thereof, and
    wherein the composition further comprises an endo-beta-galactosidase.

2. The method of claim 1, wherein the composition further comprises decorin.

3. The method of claim 1, wherein the compound modulates collagen fibrillogenesis in the skin.

4. The method of claim 1, wherein the composition modulates collagen fibrillogenesis and interfibrillar spacing, and
wherein the level of keratan sulfate in the skin is modulated by the composition.

5. The method of claim 1, wherein the composition modulates unorganized matrix deposition by fibroblasts, and
wherein the level of keratan sulfate in the skin is modulated by the composition.

6. The method of claim 4, wherein the endo-beta-galactosidase is selected from the group consisting of keratanase, keratanase II, Bc keratanase II, and combinations thereof.

7. The method of claim 5, wherein the endo-beta-galactosidase is selected from the group consisting of keratanase, keratanase II, Bc keratanase II, and combinations thereof.

8. The method of claim 1, wherein the skin condition is a skin inflammatory condition,
wherein the skin inflammatory condition is selected from the group consisting of non-allergic skin inflammatory conditions, allergic skin inflammatory conditions, neurogenic skin inflammatory conditions, UV radiation (UVR) induced skin inflammatory conditions, miscellaneous skin inflammatory conditions, and combinations thereof.

9. The method of claim 1, wherein the skin condition is a skin inflammatory condition or skin pigmentation, and
wherein the modulation of the level of FM, lumican, and/or biglycan modulates TNF-alpha activity.

10. The method of claim 1, wherein the skin condition is a skin inflammatory condition and skin pigmentation.

11. The method of claim 1, wherein the skin condition is skin pigmentation.

12. The method of claim 11, wherein the composition modulates the level of keratin sulfate.

13. The method of claim 12, wherein the endo-beta-galactosidase is selected from the group consisting of keratanase, keratanase II, Bc keratanase II, and combinations thereof.

14. The method of claim 1, wherein the compound modulates bFGF activity.

15. The method of claim 1, wherein the composition modulates skin pigmentation, wherein the modulation of the level of a SLRP selected from the group consisting of FM, lumican, biglycan and combinations thereof modulates melanocyte proliferation.

16. The method of claim 1, wherein the composition modulates skin pigmentation, wherein the compound modulates melanocyte melanin production.

17. The method of claim 1, wherein the composition modulates skin pigmentation, wherein the compound modulates stem cell factor.

18. The method of claim 1, wherein the composition is administered to the human being along with keratin sulfate.

19. The method of claim 18, wherein the SLRPs are selected from the group consisting of fibromodulin (FM), lumican, decorin, biglycan, and combinations thereof.

20. The method of claim 1, further comprising administering to the intact skin chondroitinase B; and administering to the intact skin MMP-1.

* * * * *